US008975403B2

(12) United States Patent
Inouye et al.

(10) Patent No.: US 8,975,403 B2
(45) Date of Patent: Mar. 10, 2015

(54) PROCESS FOR PRODUCING SUBSTITUTED BENZO[F]IMIDAZO[1,2-A]QUINOXALIN-3(11H)-ONES

(71) Applicants: JNC Corporation, Chiyoda-ku, Tokyo (JP); National University Corporation Tokyo Medical and Dental University, Bunkyo-ku, Tokyo (JP)

(72) Inventors: Satoshi Inouye, Kanagawa (JP); Yuiko Miura, Kanagawa (JP); Suguru Yoshida, Tokyo (JP); Takamitsu Hosoya, Tokyo (JP)

(73) Assignees: JNC Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 14/189,706

(22) Filed: Feb. 25, 2014

(65) Prior Publication Data

US 2014/0206868 A1 Jul. 24, 2014

Related U.S. Application Data

(62) Division of application No. 13/412,682, filed on Mar. 6, 2012, now Pat. No. 8,772,484.

(30) Foreign Application Priority Data

Mar. 8, 2011 (JP) .................. 2011-050487

(51) Int. Cl.
- C07D 241/36 (2006.01)
- C07D 487/04 (2006.01)
- C07D 241/38 (2006.01)
- C07D 241/44 (2006.01)
- C07D 241/54 (2006.01)

(52) U.S. Cl.
CPC ............ C07D 487/04 (2013.01); C07D 241/38 (2013.01); C07D 241/44 (2013.01); C07D 241/54 (2013.01)
USPC ...................................... 544/343

(58) Field of Classification Search
CPC ................................... C07D 241/36
USPC ......................................... 544/343
See application file for complete search history.

(56) References Cited

FOREIGN PATENT DOCUMENTS

GB 2479847 A 10/2011

OTHER PUBLICATIONS

United Kingdom Search Report dated Jun. 6, 2012 in GB Application No. 1204023.4.
Kazuki Kiyose et al., "Functional Near-Infrared Fluorescent Probes," Chem. Asian J., 2008, 3, pp. 506-515.
Osamu Shimomura et al., "Semi-synthetic aequorin, An improved tool for the measurement of calcium ion concentration," Biochem. J., 1988, 251, pp. 405-410.
Satoshi Inouye et al., "The Use of *Renilla* luciferase, *Oplophorus* luciferase, and Apoaequorin as Bioluminescent Reporter Protein in the Presence of Coelenterazine Analogues as Substrate," Biochemical and Biophysical Research Communications, 1997, 233, pp. 349-353.
Andreas Markus Loening et al., "Red-shifted *Renilla reniformis* luciferase variants for imaging in living subjects," Nature Methods, Aug. 2007, vol. 4, No. 8, pp. 641-643.
Galina A. Stepanyuk et al., "Coelenterazine-v ligated to Ca2+ -triggered coelenterazine-binding protein is a stable and efficient substrate of the red-shifted mutant of *Renilla muelleri* luciferase," Anal. Bioanal. Chem., 2010, 398, pp. 1809-1817.

*Primary Examiner* — Douglas M Willis
(74) *Attorney, Agent, or Firm* — Drinker Biddle & Reath LLP

(57) ABSTRACT

A simple process for producing v-coelenterazine compounds has been desired. Described is a process for producing a v-coelenterazine compound represented by general formula (II) comprising (1) the step of reacting a compound of general formula (VIII) with a methyltriphenylphosphonium salt in the presence of a base to give a compound represented by general formula (IX), (2) the step of performing a ring-closing metathesis reaction on any one selected from the group consisting of the compound represented by general formula (IX) and a compound of general formula (X) which is the compound of general formula (IX) wherein the amino is protected with $R^5$, and then deprotecting $R^4$ and, if any, $R^5$ to give a v-coelenteramine compound represented by general formula (XIV), and (3) the step of reacting the compound of general formula (XIV) with a compound represented by general formula (XV) to give the compound of general formula (II).

7 Claims, No Drawings

PROCESS FOR PRODUCING SUBSTITUTED BENZO[F]IMIDAZO[1,2-A]QUINOXALIN-3(11H)-ONES

This is a divisional of application Ser. No. 13/412,682, filed on Mar. 6, 2012, now U.S. Pat. No. 8,772,484, which claims the benefit of priority to Japanese Application No. 2011-050487, filed on Mar. 8, 2011, the entire contents of each of which are incorporated by reference herein in their entirety.

REFERENCE TO A SEQUENCE LISTING

A Sequence Listing containing SEQ ID NO: 1-22 is incorporated herein by reference.

TECHNICAL FIELD

The present invention relates to a process for producing v-coelenterazine compounds, and so on.

BACKGROUND

The development of new drugs is still being actively pursued all over the world, but it is difficult to conclude that new drugs could be efficiently developed as compared to the efforts involved in the development. This is believed to be due to yet insufficient understanding of biomolecular functions. In fact, even the currently available drugs remain yet unclear, in many cases, about how they act upon the body to exhibit their pharmaceutical effects. For this reason, it is required for the development of new drugs to synthesize a number of candidate compounds. Accordingly, if the details of biomolecular mechanism involved in diseases can be clarified, the development of new drugs will be greatly streamlined and such is expected to contribute to the development of a groundbreaking molecular target drug. Recently, trace analysis has become required for the same subject in animal experiments with a new drug. It has thus been strongly desired to develop a noninvasive in vivo imaging technique also from moral and ethical aspects of laboratory animals.

In recent years, as represented by green fluorescence protein (GFP), the imaging technology that visualizes molecules involved in life phenomena has been playing an important role in the medical and biological fields as an innovative technique for elucidating biomolecular functions. On the other hand, techniques for imaging the desired molecules in living animals (in vivo molecular imaging) are still less developed and, above all, it has been actively investigated to develop molecular probes available for fluorescent or luminescent imaging in the near-infrared region (wavelength of 700 nm or longer) which is able to permeate through the living tissues (K. Kiyose et al., Chem. Asian J. 2008, 3, 506).

The present inventors thought that if a practical near-infrared bioluminescence system is newly developed, a breakthrough in vivo imaging technology would be provided and have continued studies, focusing anew on coelenterazine (CTZ, 1) which is a typical bioluminescence substrate from a long time ago.

CTZ is commonly used as a luminescence substrate in many marine organisms, including photoprotein aequorin form jellyfish, Renilla luciferase from sea pansy, Gaussia luciferase from copepoda, Oplophorus luciferase from decapoda, etc. Accordingly, if a near-infrared luminescent CTZ compound (CTZ and its analogues) available for any of luciferases can be developed by modifying the structure of CTZ, it is expected that a luminescence imaging method applicable also to living animals could be provided for the detection with high sensitivity of in vivo localization of a target protein and its absolute quantity and metabolic rate, a promoter or enhancer activity of the target protein, life phenomena of a target cell accompanied by in vivo localization, etc.

Approximately 50 kinds of CTZ compounds have been synthesized so far. Some of them were examined for their substrate specificity in several bioluminescence systems.

Among them, v-coelenterazine (v-CTZ, 2) first reported by Shimomura, Kishi, et al. (O. Shimomura, Y. Kishi, et al., Biochem. J. 1988, 251, 405) was later studied for the luminescence properties of aequorin, Renilla luciferase and Oplophorus luciferase by Inouye and Shimomura. As a result, it was found that when used as a substrate for Renilla luciferase, the maximum emission wavelength was shifted toward the longer wavelength side, i.e., from 475 nm (blue emission) to 512 nm (green emission) by about 40 nm (S. Inouye & O. Shimomura, Biochem. Biophys. Res. Commun. 1997, 233, 349). It was also revealed that a part (~5%) of this emission spectrum distribution reached the near-infrared region (>700 nm).

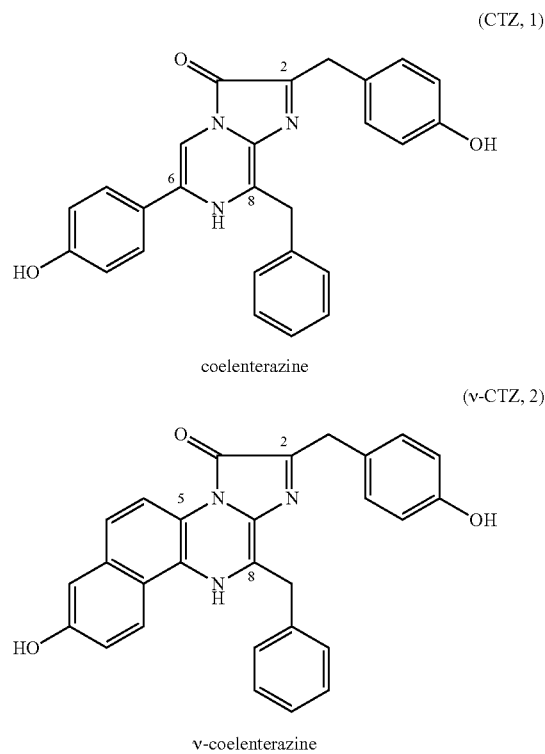

In addition, A. M. Loenig et al. recently achieved a longer wavelength shift by modifying the amino acid sequence of Renilla luciferase (A. M. Loenig et al., Nature Methods 2007, 4, 641). More specifically, they reported that the maximum emission wavelength was shifted to 547 nm (green emission) when v-CTZ was used as a substrate for the modified Renilla luciferase. In fact, they also succeeded in imaging in living mice by utilizing this luminescence system.

In order to establish a practical in vivo imaging system, however, it is desired to obtain an emission peak at a longer wavelength region. It is further pointed out that v-CTZ is easily oxidized and a problem also arises in stability (G. Stepanyuk et al., Anal. Bioanal. Chem. 2010, 398, 1809). It is therefore an important task to create a novel substrate practically applicable to the CTZ near-infrared bioluminescence system.

Furthermore, a process for producing v-CTZ has not been hitherto reported in detail, and it is also desired to establish the process.

SUMMARY

Under the foregoing circumstances, a simple process for producing v-coelenterazine compounds has been desired.

In order to solve the problems described above, the present inventors have made extensive investigations and as a result, have succeeded in developing a simple and flexible process for producing v-coelenterazine, which is applicable also to the production of a variety of v-coelenterazine analogues.

That is, the present invention provides the process for producing the following v-coelenterazine compounds, and so on.

[1] A process for producing a v-coelenteramine compound represented by general formula (XIV):

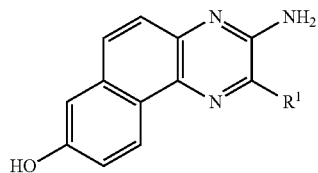

(XIV)

(wherein $R^1$ is hydrogen, a halogen, a substituted or unsubstituted hydrocarbon group, or a substituted or unsubstituted heterocyclic group), which comprises:

(1) the step of reacting a compound represented by general formula (VIII):

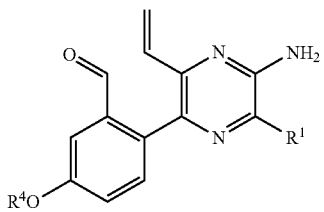

(VIII)

(wherein $R^1$ is the same as defined above and $R^4$ is a protecting group) with a methyltriphenylphosphonium salt in the presence of a base to give a compound represented by general formula (IX):

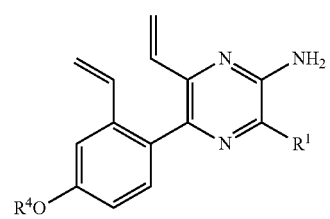

(IX)

(wherein $R^1$ and $R^4$ are the same as defined above), and, (2) the step of performing a ring-closing metathesis reaction on any one selected from the group consisting of the compound represented by general formula (IX) and a compound represented by general formula (X) which is the compound represented by general formula (IX) wherein the amino is protected with $R^5$:

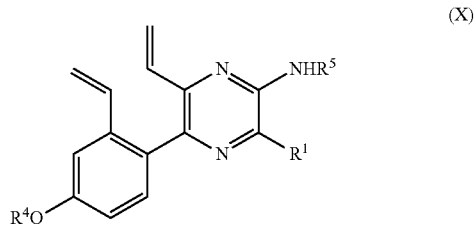

(X)

(wherein $R^1$ and $R^4$ are the same as defined above and $R^5$ is a protecting group), and then deprotecting $R^4$ and, if any, $R^5$.

[2] A process for producing a v-coelenterazine compound represented by general formula (II):

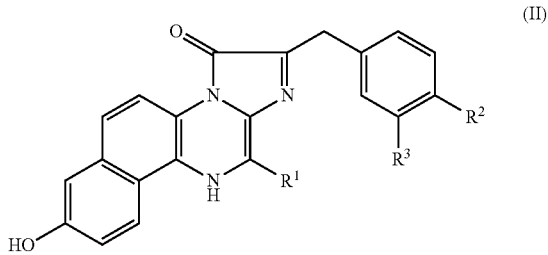

(II)

(wherein:

$R^1$ is hydrogen, a halogen, a substituted or unsubstituted hydrocarbon group, or a substituted or unsubstituted heterocyclic group, each of $R^2$ and $R^3$ independently represents hydrogen, hydroxy, an alkoxyl, a halogen, or a substituted or unsubstituted hydrocarbon group), which comprises:

(1) the step of reacting a compound represented by general formula (VIII):

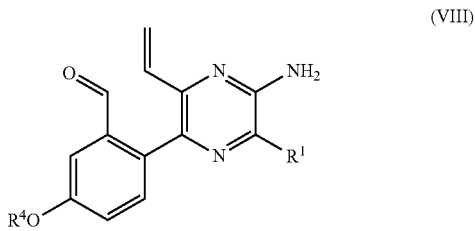

(VIII)

(wherein $R^1$ is the same as defined above and $R^4$ is a protecting group) with a methyltriphenylphosphonium salt in the presence of a base to give a compound represented by general formula (IX):

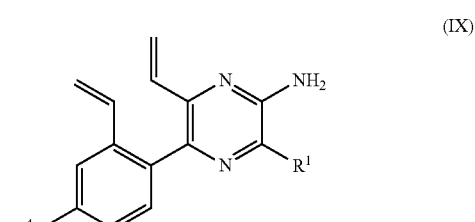

(IX)

(wherein $R^1$ and $R^4$ are the same as defined above), (2) the step of performing a ring-closing metathesis reaction on any one selected from the group consisting of the compound represented by general formula (IX) and a compound represented by general formula (X) which is the compound represented by general formula (IX) wherein the amino is protected with $R^5$:

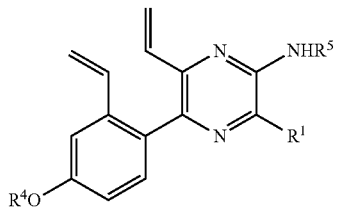

(wherein $R^1$ and $R^4$ are the same as defined above and $R^5$ is a protecting group), and then deprotecting $R^4$ and if any, $R^5$ to give a v-coelenteramine compound represented by general formula (XIV):

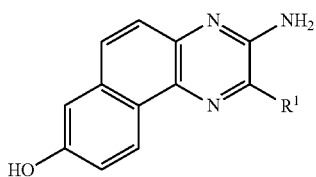

(wherein $R^1$ is the same as defined above), and, (3) the step of reacting the compound represented by general formula (XIV) with a compound represented by general formula (XV):

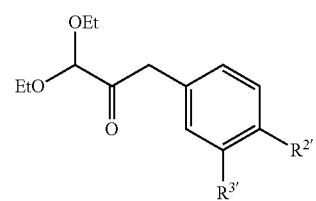

(wherein each of $R^{2'}$ and $R^{3'}$ independently represents hydrogen, hydroxy, an alkoxyl, a halogen, a hydrocarbon group, or a hydroxy group protected with a protecting group) to give the compound represented by general formula (II).

[3] The method according to [1] or [2] described above, wherein at least one base selected from the group consisting of n-butyl lithium, potassium tert-butoxide, sodium methoxide, sodium ethoxide and lithium diisopropylamide is used as the base in the step (1) above.

[4] The method according to any one of [1] to [3] described above, wherein at least one solvent selected from the group consisting of tetrahydrofuran, diethyl ether, cyclopropyl methyl ether, tert-butyl methyl ether, dioxane and toluene is used in the step (1) above.

[5] The method according to any one of [1] to [4] above, wherein the reaction temperature and reaction time in the step (1) above are set at 0° C. to 40° C. for an hour to 4 hours.

[6] The method according to any one of [1] to [5] above, wherein a Hoveyda-Grubbs second generation catalyst is used as the catalyst for the ring-closing metathesis reaction in the step (2) above.

[7] The method according to any one of [1] to [6] above, wherein at least one solvent selected from the group consisting of dichloroethane, dichloromethane, chloroform, trichloroethane, tetrachloroethane, benzene, toluene, xylene, monochlorobenzene, dichlorobenzene, hexane, heptane, octane, tetrahydrofuran, dioxane, diethyl ether, dibutyl ether, diisopropyl ether and dimethoxyethane.

[8] The method according to any one of [1] to [7] above, wherein the reaction temperature and reaction time of the ring-closing metathesis reaction in the step (2) above are set at 25° C. to 110° C. for an hour to 48 hours.

[9] The method according to any one of [1] to [8] above, wherein $R^1$ is hydrogen, a halogen, a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, a heterocyclic group, or an alkynyl which may optionally be substituted with an alicyclic group, in the formulae above.

[10] The method according to any one of [1] to [9] above, wherein each of $R^2$ and $R^3$ independently represents hydrogen, hydroxy, a halogen, an alkyl having 1 to 4 carbon atoms which may optionally substituted with an alicyclic group, trifluoromethyl or an alkoxyl, in the formula above.

[11] The method according to any one of [1] to [10] above, wherein $R^4$ is methyl, methoxymethyl, tetrahydropyranyl, benzyl, 4-methoxybenzyl, tert-butyldimethylsilyl, trimethylsilyl, triethylsilyl, phenyldimethylsilyl, tert-butyldiphenylsilyl or triisopropylsilyl, in the formulae above.

[12] The method according to any one of [1] to [11] above, wherein $R^5$ is acetyl, benzoyl, p-tosyl, tert-butoxycarbonyl or benzyloxycarbonyl, in the formulae above.

[13] The method according to any one of [2] to [12] above, wherein each of the protecting groups for the hydroxy groups for $R^{2'}$ and $R^{3'}$ independently represents tert-butyldimethylsilyl, methoxymethyl, tetrahydropyranyl, trimethylsilyl, phenyldimethylsilyl, triethylsilyl, phenyldimethylsilyl, tert-butyldiphenylsilyl or triisopropylsilyl, in the formula above.

[14] The method according to any one of [1] to [13] above, wherein the compound represented by general formula (VIII) above is obtained by:

(1) reacting 2-amino-3,5-dibromo-6-chloropyrazine with $R^1MgX$ (wherein $R^1$ is the same as defined above and X is a halogen) and $ZnCl_2$ in the presence of a palladium catalyst to give the compound represented by general formula (V):

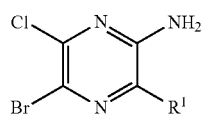

(wherein $R^1$ is the same as defined above), (2) reacting the compound represented by general formula (V) above with a compound represented by general formula (VI):

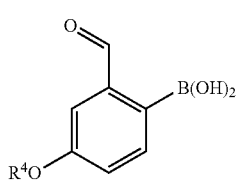

(wherein $R^4$ is the same as defined above), in the presence of a palladium catalyst and a base to give the compound represented by general formula (VII):

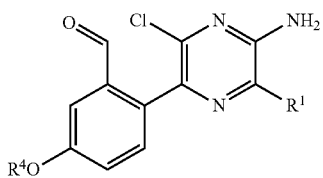

(wherein $R^1$ and $R^4$ are the same as defined above), and, (3) reacting the compound represented by general formula (VII) with tributyl(vinyl)tin in the presence of a palladium catalyst.

According to the present invention, there is provided a process for producing the v-coelenterazine compounds in a simple manner. In a preferred embodiment of the present invention, the v-coelenterazine compounds can be produced in a high yield.

DETAILED DESCRIPTION

Hereinafter, the present invention is described in detail.

1. v-Coelenterazine Compound

The present invention provides the compounds represented by general formula (II) below (v-coelenterazine compounds of the present invention).

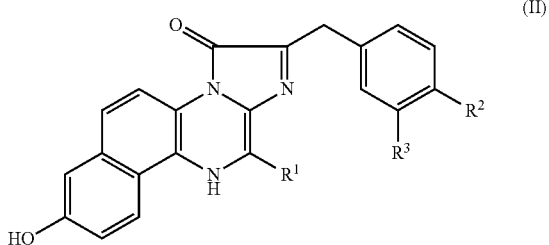

In the formula:

$R^1$ is hydrogen, a halogen, a substituted or unsubstituted hydrocarbon group, or a substituted or unsubstituted heterocyclic group, each of $R^2$ and $R^3$ independently represents hydrogen, hydroxy, an alkoxyl, a halogen, or a substituted or unsubstituted hydrocarbon group.

In a preferred embodiment of the present invention, the substituted or unsubstituted hydrocarbon group and the substituted or unsubstituted heterocyclic group in $R^1$ to $R^3$ do not substantially inhibit any of the reactions in the process for producing the v-coelenterazine compounds or v-coelenteramine compounds of the present invention.

In a further preferred embodiment of the present invention, in the formulae described above, $R^1$ is hydrogen, a halogen, a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, a heterocyclic group or an alkynyl which may optionally be substituted with an alicyclic group, and, each of $R^2$ and $R^3$ independently represents hydrogen, hydroxy, a halogen, an alkyl having 1 to 4 carbon atoms which may optionally substituted with an alicyclic group, trifluoromethyl or an alkoxyl.

The "halogen" for $R^1$ includes, for example, fluorine, chlorine, bromine and iodine. In a preferred embodiment of the present invention, the "halogen" is fluorine.

The "substituted or unsubstituted aryl" for $R^1$ includes, for example, an aryl having 1 to 5 substituents or an unsubstituted aryl. The substituent is at least one selected from the group consisting of a halogen (fluorine, chlorine, bromine, iodine, etc.), hydroxy, an alkyl having 1 to 6 carbon atoms, an alkoxyl having 1 to 6 carbon atoms, an amino, a dialkylamino having 1 to 6 carbon atoms, and the like. In some embodiments of the present invention, the substituent is hydroxy. Specific examples of the "substituted or unsubstituted aryl" include phenyl, p-hydroxyphenyl, p-aminophenyl, p-dimethylaminophenyl, etc. In some embodiments of the present invention, the "substituted or unsubstituted aryl" is an unsubstituted aryl, e.g., phenyl, etc.

The "substituted or unsubstituted arylalkyl" for $R^1$ includes, for example, an arylalkyl having 7 to 10 carbon atoms which contains 1 to 5 substituents, or an unsubstituted arylalkyl having 7 to 10 carbon atoms. Examples of the substituent are a halogen (fluorine, chlorine, bromine, iodine, etc.), hydroxy, an alkyl having 1 to 6 carbon atoms, an alkoxyl having 1 to 6 carbon atoms, an amino, a dialkylamino having 1 to 6 carbon atoms, and the like. The "substituted or unsubstituted arylalkyl" includes, for example, benzyl, α-hydroxybenzyl, phenylethyl, p-hydroxybenzyl, p-dimethylaminobenzyl, etc., preferably, benzyl, α-hydroxybenzyl, phenylethyl, etc. In some embodiments of the present invention, the "substituted or unsubstituted arylalkyl" is benzyl.

The "substituted or unsubstituted arylalkenyl" for $R^1$ includes, for example, an arylalkenyl having 8 to 10 carbon atoms which contain 1 to 5 substituents, or an unsubstituted arylalkenyl having 8 to 10 carbon atoms. Examples of the substituent are a halogen (fluorine, chlorine, bromine, iodine, etc.), hydroxy, an alkyl having 1 to 6 carbon atoms, an alkoxyl having 1 to 6 carbon atoms, an amino, a dialkylamino having 1 to 6 carbon atoms, and the like. Examples of the "substituted or unsubstituted arylalkenyl" include phenylvinyl, p-hydroxyphenylvinyl, p-dimethylaminophenylvinyl, etc. In some embodiments of the present invention, the "substituted or unsubstituted arylalkenyl" is an unsubstituted arylalkenyl, e.g., phenylvinyl, etc.

The "alkyl which may optionally be substituted with an alicyclic group" for $R^1$ is, for example, an unsubstituted straight or branched alkyl having 1 to 4 carbon atoms, or an unsubstituted straight or branched alkyl having 1 to 4 carbon atoms which is substituted with, e.g., 1 to 10 alicyclic groups. Examples of the alicyclic group are cyclohexyl, cyclopentyl, adamantyl, cyclobutyl, cyclopropyl, etc. Preferably, the alicyclic group is cyclohexyl, cyclopentyl, adamantyl, etc. Examples of the "alkyl which may optionally be substituted with an alicyclic group" are methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group, and examples include methyl, ethyl, propyl, adamantylmethyl, cyclopentylmethyl, cyclohexylmethyl, cyclohexylethyl, etc.

The "alkenyl which may optionally be substituted with an alicyclic group" for $R^1$ is an unsubstituted straight or branched alkenyl having 2 to 6 carbon atoms, or a straight or branched alkenyl having 2 to 6 carbon atoms which is substituted with, e.g., 1 to 10 alicyclic groups. Examples of the alicyclic group are cyclohexyl, cyclopentyl, adamantyl, cyclobutyl, cyclopropyl, etc. Preferably, the alicyclic group is cyclohexyl, cyclopentyl, adamantyl, etc. Examples of the "alkenyl which may optionally be substituted with an alicyclic group" include vinyl, 1-propenyl, 2-propenyl, 1-butenyl, 2-butenyl, 3-butenyl, 2-methylpropenyl, etc., preferably, 2-methylpropenyl, etc.

Examples of the "alicyclic group" for $R^1$ include cyclohexyl, cyclopentyl, adamantyl, cyclobutyl, cyclopropyl, etc. Preferably, the alicyclic group is cyclohexyl, etc.

The "heterocyclic group" for $R^1$ is, for example, a group formed by a 5- to 7-membered ring containing 1 to 3 atoms selected from the group consisting of N, O and S as the atoms for forming the ring, in addition to carbons and bound through carbon, a group formed by condensing at least two such rings and bound through carbon, or a group formed by condensing such rings with a benzene ring and bound through carbon. Examples of the "heterocyclic group" are thiophen-2-yl, 2-furanyl, 4-pyridyl, etc. In some embodiments of the present invention, the "heterocyclic group" is a heterocyclic group containing sulfur, e.g., thiophen-2-yl.

The "alkynyl which may optionally be substituted with an alicyclic group" for $R^1$ is an unsubstituted straight or branched alkynyl having 2 to 6 carbon atoms, or a substituted straight or branched alkynyl having 2 to 6 carbon atoms which is optionally substituted with, e.g., 1 to 10 alicyclic groups. Examples of the alicyclic group are cyclohexyl, cyclopentyl, adamantyl, cyclobutyl, cyclopropyl, etc. Preferably, the alicyclic group is cyclohexyl, cyclopentyl, adamantyl, etc. Examples of the "alkynyl which may optionally be substituted with an alicyclic group" are ethynyl, propynyl, butynyl, 2-methylpropynyl, etc., preferably, 2-methylpropynyl, etc.

In a preferred embodiment of the present invention, $R^1$ is phenyl, p-hydroxyphenyl, benzyl, α-hydroxybenzyl, phenylethyl, phenylvinyl, cyclohexyl, cyclohexylmethyl, cyclohexylethyl, methyl, ethyl, propyl, 2-methylpropyl, 2-methylpropenyl, adamantylmethyl, cyclopentylmethyl or thiophen-2-yl. In a more preferred embodiment of the present invention, $R^1$ is benzyl.

The "halogen" for $R^2$ includes, for example, fluorine, chlorine, bromine and iodine. In a preferred embodiment of the present invention, the "halogen" is fluorine.

The "alkyl having 1 to 4 carbon atoms which may optionally be substituted with an aliphatic group" for $R^2$ is, for example, an unsubstituted straight or branched alkyl having 1 to 4 carbon atoms or a straight or branched alkyl having 1 to 4 carbon atoms which is substituted with, e.g., 1 to 10 alicyclic groups. Examples of the alicyclic group are cyclohexyl, cyclopentyl, adamantyl, cyclobutyl, cyclopropyl, etc. Preferably, the alicyclic group is cyclohexyl, cyclopentyl, adamantyl, etc. Examples of the "alkyl which may optionally be substituted with an alicyclic group" are methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group, and examples include methyl, ethyl, propyl, adamantylmethyl, cyclopentylmethyl, cyclohexylmethyl, cyclohexylethyl, etc.

The "alkoxyl" for $R^2$ includes, for example, a straight or branched alkoxy having 1 to 6 carbon atoms. Examples of the "alkoxy" are methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, 1,1-dimethylpropyloxy, 1,2-dimethylpropoxy, 2,2-dimethylpropyloxy, n-hexoxy, 1-ethylpropoxy, 2-ethylpropoxy, 1-methylbutoxy, 2-methylbutoxy, iso-hexoxy, 1-methyl-2-ethylpropoxy, 1-ethyl-2-methylpropoxy, 1,1,2-trimethylpropoxy, 1,1,2-trimethylpropoxy, 1-propylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy, hexyloxy, etc. In some embodiments of the present invention, the "alkoxy" is methoxy, ethoxy, n-propoxy, iso-propoxy, sec-propoxy, n-butoxy, iso-butoxy, sec-butoxy, tert-butoxy, etc., preferably, methoxy.

In a preferred embodiment of the present invention, $R^2$ is hydrogen, hydroxy, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy. In a more preferred embodiment of the present invention, $R^2$ is hydroxy or trifluoromethyl.

The "halogen" for $R^3$ includes, for example, fluorine, chlorine, bromine and iodine. In a preferred embodiment of the present invention, the "halogen" is fluorine.

The "alkyl having 1 to 4 carbon atoms which may optionally be substituted with an alicyclic group" for $R^3$ includes, for example, an unsubstituted straight or branched alkyl having 1 to 4 carbon atoms or a substituted straight or branched alkyl having 1 to 4 carbon atoms which is substituted with, e.g., 1 to 10 alicyclic groups. Examples of the alicyclic group are cyclohexyl, cyclopentyl, adamantyl, cyclobutyl, cyclopropyl, etc. Preferably, the alicyclic group is cyclohexyl, cyclopentyl, adamantyl, etc. Examples of the "alkyl which may optionally be substituted with an alicyclic group" are methyl, ethyl, propyl, 2-methylpropyl, adamantylmethyl, cyclopentylmethyl, cyclohexylmethyl, cyclohexylethyl, cyclobutylmethyl, cyclopropylmethyl, etc., preferably, methyl, ethyl, propyl, 2-methylpropyl, adamantylmethyl, cyclopentylmethyl, cyclohexylmethyl, cyclohexylethyl, etc. In some embodiments of the present invention, the "alkyl which may optionally be substituted with an alicyclic group" is a straight alkyl which may optionally be substituted with an alicyclic group, and examples include methyl, ethyl, propyl, adamantylmethyl, cyclopentylmethyl, cyclohexylmethyl, cyclohexylethyl, etc.

The "alkoxyl" for $R^3$ includes, for example, a straight or branched "alkoxy" having 1 to 6 carbon atoms and examples of the "alkoxy" are methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, 1,1-dimethylpropyloxy, 1,2-dimethylpropoxy, 2,2-dimethylpropyloxy, n-hexoxy, 1-ethylpropoxy, 2-ethylpropoxy, 1-methylbutoxy, 2-methylbutoxy, iso-hexoxy, 1-methyl-2-ethylpropoxy, 1-ethyl-2-methylpropoxy, 1,1,2-trimethylpropoxy, 1,1,2-trimethylpropoxy, 1-propylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy, hexyloxy, etc. In some embodiments of the present invention, the "alkoxy" includes methoxy, ethoxy, n-propoxy, iso-propoxy, sec-propoxy, n-butoxy, iso-butoxy, sec-butoxy, tert-butoxy, and preferably, methoxy.

In a preferred embodiment of the present invention, $R^3$ is hydrogen, hydroxy, fluorine, methyl, ethyl, propyl, adamantylmethyl, cyclopentylmethyl, cyclohexylmethyl, cyclohexylethyl, trifluoromethyl, methoxy, ethoxy, n-propoxy, iso-propoxy, sec-propoxy, n-butoxy, iso-butoxy, sec-butoxy or tert-butoxy. In a more preferred embodiment of the present invention, $R^3$ is hydrogen.

In some embodiments of the present invention, in the general formula (II):

$R^1$ is benzyl, $R^2$ is hydroxy or trifluoromethyl, and, $R^3$ is hydrogen.

In a certain embodiment of the present invention, the compound represented by general formula (II) is the compound represented by the formula described below (v-coelenterazine).

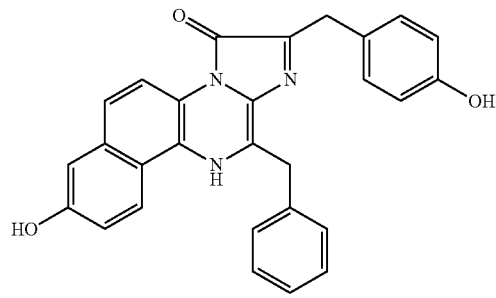

In another embodiment of the present invention, the compound represented by general formula (II) is the compound represented by the following formula (cf3-v-coelenterazine).

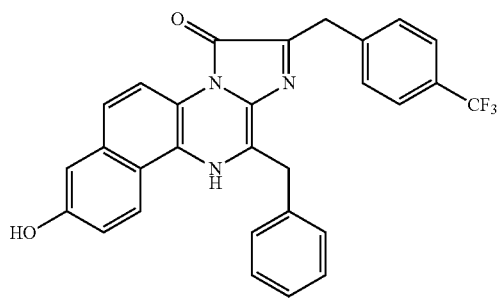

The present invention further provides the compounds represented by general formula (XIV) below (the v-coelenteramine compounds of the present invention):

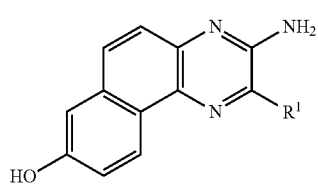

(XIV)

(wherein $R^1$ is the same as described for the general formula (II) above).

In a certain embodiment of the present invention, the compound represented by general formula (XIV) is the compounds represented by the following formula (v-coelenteramine).

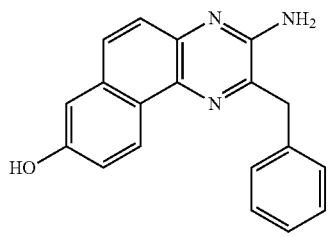

2. Process for Producing v-Coelenteramine Compounds or v-Coelenterazine Compounds of the Invention The process for producing the compound represented by general formula (XIV) (process for producing the v-coelenteramine compounds of the present invention) and the process for producing the compound represented by general formula (II) (process for producing the v-coelenterazine compounds of the present invention) are described below.

In the production processes described below, $R^1$ to $R^3$ are the same as described above.

Each of $R^{2'}$ and $R^{3'}$ independently represents hydrogen, hydroxy, an alkoxyl, a halogen, a substituted or unsubstituted hydrocarbon group or a protected hydroxy, etc. The protecting group in the "hydroxy protected with a protecting group" for $R^{2'}$ and $R^{3'}$ is, for example, tert-butyldimethylsilyl, methoxymethyl, tetrahydropyranyl, trimethylsilyl, triethylsilyl, phenyldimethylsilyl, tert-butyldiphenylsilyl or triisopropylsilyl, preferably, tert-butyldimethylsilyl.

The "alkoxyl," "halogen" and "substituted or unsubstituted hydrocarbon group" for $R^{2'}$ and $R^{3'}$ are the same as described for $R^2$ and $R^3$.

Preferably, $R^{2'}$ is tert-butyldimethylsilyloxy. Preferably, $R^{3'}$ is hydrogen.

$R^4$ is a protecting group, e.g., methyl, methoxymethyl, tetrahydropyranyl, benzyl, 4-methoxybenzyl, tert-butyldimethylsilyl, trimethylsilyl, triethylsilyl, phenyldimethylsilyl, tert-butyldiphenylsilyl or triisopropylsilyl, and preferably, methyl.

$R^5$ is a protecting group, e.g., acetyl, benzoyl, p-tosyl, tert-butoycarbonyl or benzyloxycarbonyl. Preferably, $R^5$ is acetyl.

X is a halogen, e.g., fluorine ($F^-$), chlorine ($Cl^-$), bromine ($Br^-$) or iodine ($I^-$). Preferably, X is bromine ($Br^-$).

2.1. Process for Producing the Compound Represented by General Formula (XIV)

The compound represented by general formula (XIV) can be produced from the compound represented by general formula (VIII) as follows.

(1) In the first step, the formyl in the compound represented by general formula (VIII) is methylated via a Wittig reaction. More specifically, the compound represented by general formula (VIII) is reacted with a methyltriphenylphosphonium salt ($Ph_3P^+CH_3X^-$) in the presence of a base to give the compound represented by general formula (IX).

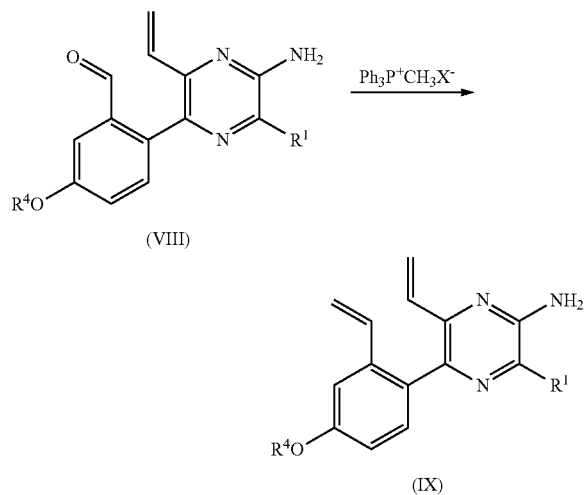

(VIII)

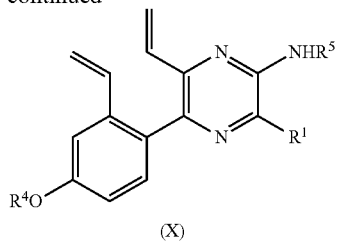

(IX)

The methyltriphenylphosphonium salt is preferably methyltriphenylphosphonium bromide.

Specific examples of the base used in the Wittig reaction are n-butyl lithium (n-BuLi), potassium tert-butoxide, sodium methoxide, sodium ethoxide, lithium diisopropylamide, etc.

Specific examples of the solvents used in the reaction include tetrahydrofuran, diethyl ether, cyclopropyl methyl ether, tert-butyl methyl ether, dioxane, toluene, etc. These solvents may be appropriately chosen and used alone or as a solvent mixture thereof.

The reaction temperature and reaction time are not particularly limited and are, e.g., at 0° C. to 40° C. for an hour to 4 hours, preferably, at 10° C. to 30° C. for an hour to 3 hours, and more preferably, at 10° C. to 20° C. for an hour to 2 hours.

(2) In the next step, any one selected from the group consisting of the compound represented by general formula (IX) and the compound represented by general formula (X) in which the amino in the compound represented by general formula (IX) is protected with $R^5$ is subjected to the ring-closing metathesis reaction followed by deprotecting $R^4$ and, if any, $R^5$. Thus, the compound represented by general formula (XIV) is obtained.

(2-1) When the compound represented by general formula (X) is subjected to the subsequent ring-closing metathesis reaction, the amino in the compound represented by general formula (IX) is first protected with $R^5$ to give the compound represented by general formula (X).

(IX)

(X)

Specifically, protection of the amino with $R^5$ is performed as follows. The compound represented by general formula (IX) is reacted with acetyl chloride, acetic anhydride, benzoyl chloride, di-t-butyl dicarbonate, benzyl chloroformate, etc. in the presence of a base such as triethylamine, diisopropylethylamine, pyridine and 4-dimethylaminopyridine. More specifically, the compound represented by general formula (X) wherein $R^5$ is acetyl can be obtained by the process described in SYNTHESIS EXAMPLES later described.

Specific examples of the solvents used in the reaction include pyridine, methylene chloride, tetrahydrofuran, toluene, etc. These solvents may be appropriately chosen and used alone or as a solvent mixture thereof.

The reaction temperature and reaction time are not particularly limited and are, e.g., at 0° C. to 100° C. for an hour to 24 hours, preferably, at 20° C. to 70° C. for an hour to 12 hours, and more preferably, at 50° C. to 60° C. for an hour to 2 hours.

(2-2) Subsequently, any one selected from the group consisting of the compound represented by general formula (IX) and the compound represented by general formula (X) is subjected to the ring-closing metathesis reaction to give a tricyclic aromatic compound. More specifically, the ring-closing metathesis reaction of the compound represented by general formula (IX) or the compound represented by general formula (X) is carried out in the presence of a Grubbs catalyst or a Hoveyda-Grubbs catalyst to give the compound represented by general formula (XI') or the compound represented by general formula (XI).

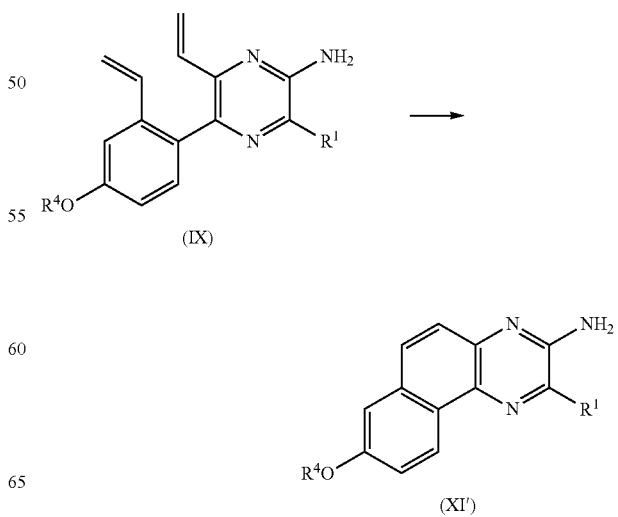

(IX)

(XI')

-continued

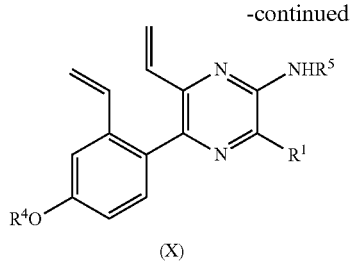

(X)

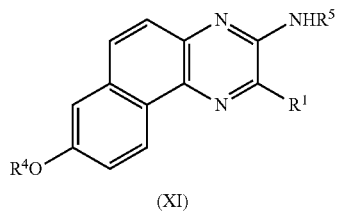

(XI)

In a preferred embodiment of the present invention, the compound represented by general formula (X) is used as the compound provided for the ring-closing metathesis. By using the compound represented by general formula (X), the compound represented by general formula (XI) can be obtained in a good yield.

The Grubbs catalyst or the Hoveyda-Grubbs catalyst used in the ring-closing metathesis reaction includes a Grubbs first generation catalyst, a Grubbs second generation catalyst, a Hoveyda-Grubbs first generation catalyst, a Hoveyda-Grubbs second generation catalyst, etc., and preferably, a Hoveyda-Grubbs second generation catalyst.

Specific examples of the solvents used in the reaction include dichloroethane, dichloromethane, chloroform, trichloroethane, tetrachloroethane, benzene, toluene, xylene, monochlorobenzene, dichlorobenzene, hexane, heptane, octane, tetrahydrofuran, dioxane, diethyl ether, dibutyl ether, diisopropyl ether, dimethoxyethane, etc. These solvents may be appropriately chosen and used alone or as a solvent mixture thereof.

The reaction temperature and reaction time are not particularly limited and are, e.g., at 25° C. to 110° C. for an hour to 48 hours, preferably, at 50° C. to 110° C. for an hour to 24 hours, and more preferably, at 90° C. to 100° C. for 12 to 18 hours.

(2-3) After the compound represented by general formula (XI') is obtained in (2-2) above, $R^4$ in the compound represented by general formula (XI') is deprotected to give the compound represented by general formula (XIV).

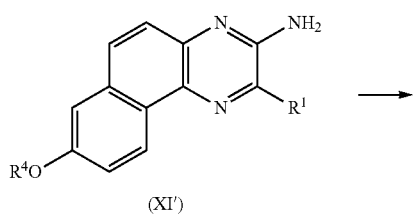

(XI')

Specifically, $R^4$ is deprotected as follows. The deprotection is effected through the reaction with a Lewis acid or a Brønsted acid. More specifically, the deprotection of $R^4$ which is methyl can be performed by the procedures described in SYNTHESIS EXAMPLES later given.

Specific examples of the solvents used in the reaction include pyridine, tetrahydrofuran, toluene, dimethylformamide, dimethylsulfoxide, water, etc. These solvents may be appropriately chosen and used alone or as a solvent mixture thereof, or may not be used.

The reaction temperature and reaction time are not particularly limited and are, e.g., at 0° C. to 300° C. for 0.1 to 60 hours, preferably, at 30° C. to 250° C. for 0.5 to 12 hours, and more preferably, at 180° C. to 220° C. for 0.5 to an hour.

(2-4) On the other hand, when the compound represented by general formula (XI) is obtained in (2-2) above, $R^4$ in the compound represented by general formula (XI) is deprotected to give the compound represented by general formula (XIII)

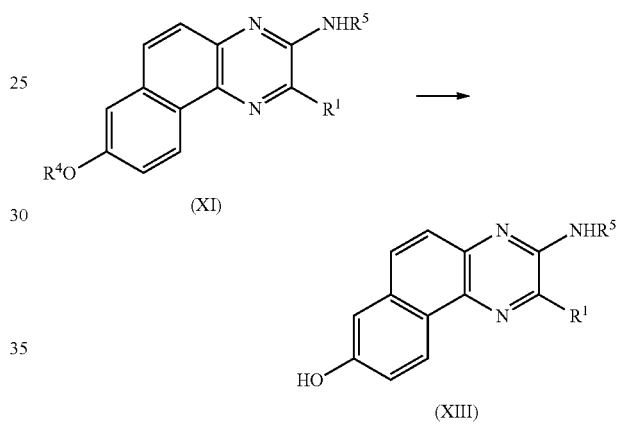

(XI)

(XIII)

Specifically, $R^4$ is deprotected as follows. The deprotection is effected by the reaction with a Lewis acid or a Brønsted acid. More specifically, the deprotection of $R^4$ which is methyl can be performed by the procedures described in SYNTHESIS EXAMPLES later given.

Specific examples of the solvents used in the reaction include dichloromethane, tetrahydrofuran, diethyl ether, dioxane, methanol, etc. These solvents may be appropriately chosen and used alone or as a solvent mixture thereof.

The reaction temperature and reaction time are not particularly limited and are, e.g., at 0° C. to 50° C. for an hour to 24 hours, preferably, at 0° C. to 30° C. for 2 to 6 hours, and more preferably, at 0° C. to 20° C. for 2 to 4 hours.

(2-5) Furthermore, $R^5$ in the compound represented by general formula (XIII) is deprotected to give the compound represented by general formula (XIV).

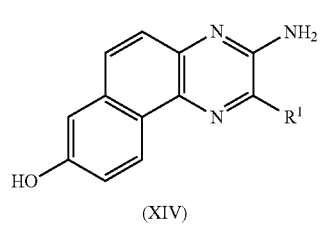

(XIV)

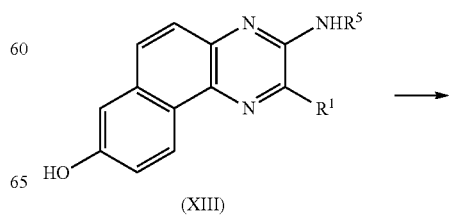

(XIII)

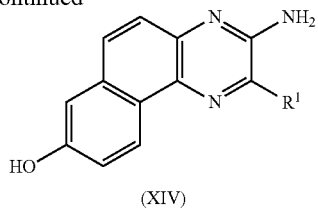

Specifically, R⁵ is deprotected as follows. The deprotection is effected by heating in a solvent in the presence of a base such as sodium hydrogencarbonate, potassium carbonate, etc. More specifically, the deprotection of $R^5$ which is acetyl can be performed by the procedures described in SYNTHESIS EXAMPLES later given.

Specific examples of the solvents used in the reaction include methanol, ethanol, n-butanol, t-butanol, dioxane, tetrahydrofuran, water, etc. These solvents may be appropriately chosen and used alone or as a solvent mixture thereof.

The reaction temperature and reaction time are not particularly limited and are, e.g., at 40° C. to 100° C. for an hour to 24 hours, preferably, at 50° C. to 80° C. for 2 to 24 hours, and more preferably, at 60° C. to 70° C. for 12 to 16 hours.

2.2. Process for Producing the Compound Represented by General Formula (II)

The compound represented by general formula (II) can be produced from the compound represented by general formula (VIII) as follows.

(1) The compound represented by general formula (XIV) is produced as described above.

(2) Then, the compound represented by general formula (XIV) is reacted with the compound represented by general formula (XV) to give the compound represented by general formula (II).

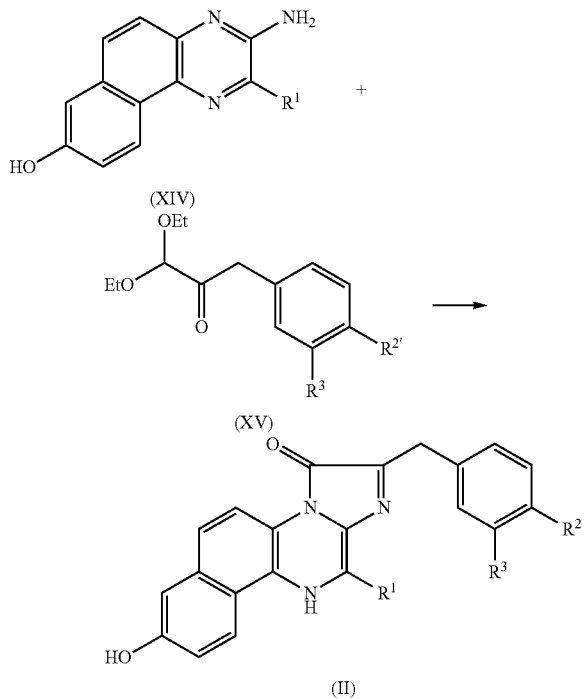

The compound represented by general formula (XV) can be produced by known processes. Specifically, the compound can be produced by the processes described in Adamczyk, M. et al., *Synth. Commun.*, 32, 3199-3205 (2002) or Baganz, H. & May, H.-J. *Chem. Ber.*, 99, 3766-3770 (1966) and Baganz, H. & May, H.-J. *Angew. Chem., Int. Ed. Eng.*, 5, 420 (1966), or modifications thereof. More specifically, the compound represented by general formula (XV) can be produced by reacting a substituted benzyl Grignard reagent with ethyl diethoxyacetate at a low temperature (−78° C.) or by reacting an α-diazo-α'-substituted phenyl ketone with tert-butyl hypochlorite in ethanol.

The solvent used in the reaction to obtain the compound represented by general formula (II) is not particularly limited but various solvent can be used. Examples are dioxane, tetrahydrofuran, ether, methanol, ethanol, water, etc. They may be used alone or as an admixture thereof.

The reaction temperature and reaction time are not particularly limited and are, e.g., at 0° C. to 200° C. for an hour to 96 hours, at room temperature to 150° C. for 3 to 72 hours, or at 60° C. to 120° C. for 6 to 24 hours.

2.3. Process for Producing the Compound Represented by General Formula (VIII)

The compound represented by general formula (VIII) above can be produced from, e.g., the compound represented by general formula (IV), as follows.

(1) In the first step, the Negishi coupling is performed on the compound represented by general formula (IV) with an organic zinc compound. Specifically, the compound represented by general formula (IV) is reacted with $R^1MgX$ and $ZnCl_2$ in the presence of a palladium catalyst to give the compound represented by general formula (V).

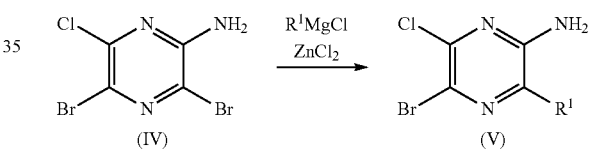

The compound represented by general formula (IV) is the compound described in WO 2003/059893 and may be synthesized, e.g., by the procedures described in SYNTHESIS EXAMPLES later given.

$R^1MgCl$ used may be synthesized by known synthesis methods or may be commercially available.

Specific examples of the palladium catalyst used for the Negishi coupling include $Pd(PPh_3)_4$, $PdCl_2(PPh_3)_2$, $Pd(OAc)_2$, tris(dibenzylideneacetone)dipalladium(0), tris(dibenzylideneacetone)dipalladium(0) chloroform complex, bis(dibenzylideneacetone)palladium(0), bis(tri-t-butylphosphino)palladium(0), (1,1'-bis(diphenylphosphino)ferrocene)dichloropalladium(II), etc.

Specific examples of the solvents used in the reaction are benzene, toluene, xylene, N,N-dimethylformamide, tetrahydrofuran, diethyl ether, t-butyl methyl ether, 1,4-dioxane, etc. These solvents may be appropriately chosen and used alone or as a solvent mixture thereof.

The reaction temperature and reaction time are not particularly limited and are, e.g., at 0° C. to 50° C. for an hour to 24 hours, preferably, at 10° C. to 40° C. for 2 to 24 hours, and more preferably, at 20° C. to 30° C. for 6 to 16 hours.

(2) In the next step, the compound represented by general formula (V) is arylated at the 5-position selectively via the Suzuki-Miyaura coupling with boronic acid. Specifically, the compound represented by general formula (V) is reacted with the compound represented by general formula (VI) in the presence of a palladium catalyst and a base to give the compound represented by general formula (VII).

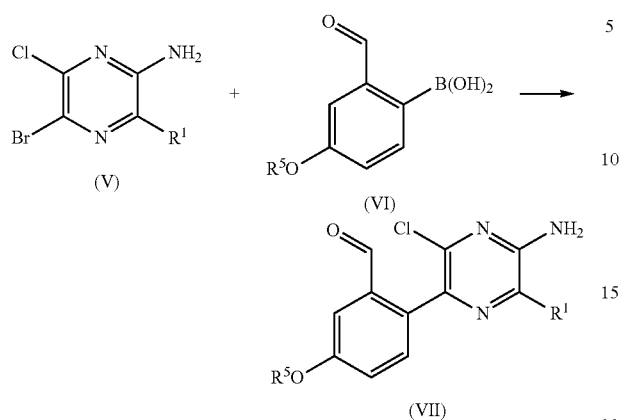

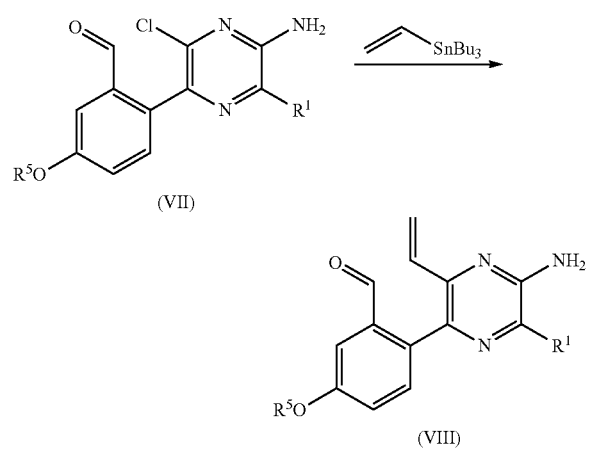

The compound represented by general formula (VI) used may be commercially available or may be synthesized by known synthesis methods.

Specific examples of the palladium catalyst used in the Suzuki-Miyaura coupling are allylpalladium(II) chloride (dimer), Pd(PPh$_3$)$_4$, PdCl$_2$(PPh$_3$)$_2$, Pd(OAc)$_2$, tris(dibenzylideneacetone)dipalladium(0), tris(dibenzylideneacetone)dipalladium(0) chloroform complex, bis(dibenzylideneacetone)palladium(0), etc.

Phosphine compounds may be added to these palladium catalyst, if necessary, to accelerate the reaction. Specific examples of the phosphine compounds are 2-(di-t-butylphosphino)-1-phenylindole, tri(t-butyl)phosphine, tricyclohexylphosphine, 1-(N,N-dimethylaminomethyl)-2-(di-t-butylphosphino)ferrocene, 1-(N,N-dibutylaminomethyl)-2-(di-t-butylphosphino)ferrocene, 1-(methoxymethyl)-2-(di-t-butylphosphino)ferrocene, 1,1'-bis(di-t-butylphosphino) ferrocene, 2,2'-bis(di-t-butylphosphino)-1,1'-binaphthyl, 2-methoxy-2'-(di-t-butylphosphino)-1,1'-binaphthyl, 2-dicyclohexylphosphino-2',6'-dimethoxybiphenyl, etc.

Specific examples of the base used in the reaction include sodium carbonate, potassium carbonate, cesium carbonate, sodium hydrogencarbonate, sodium hydroxide, potassium hydroxide, barium hydroxide, sodium ethoxide, sodium t-butoxide, sodium acetate, tripotassium phosphate, potassium fluoride, etc.

Specific examples of the solvents used in the reaction are benzene, toluene, xylene, N,N-dimethylformamide, tetrahydrofuran, diethyl ether, t-butyl methyl ether, 1,4-dioxane, methanol, ethanol, isopropyl alcohol, water, etc. These solvents may be appropriately chosen and used alone or as a solvent mixture thereof.

The reaction temperature and reaction time are not particularly limited and are, e.g., at 0° C. to 50° C. for an hour to 24 hours, preferably, at 10° C. to 40° C. for 2 to 24 hours, and more preferably, at 20° C. to 30° C. for 6 to 16 hours.

(3) In the next step, the 6-position of the pyrazine ring in the compound represented by general formula (VII) is vinylated through the Stille coupling with a vinyl compound. Specifically, the compound represented by general formula (VII) is reacted with tributyl(vinyl)tin in the presence of a palladium catalyst to give the compound represented by general formula (VIII).

Tributyl(vinyl)tin used may be commercially available or may be synthesized by known methods.

Specific examples of the palladium catalyst used in the Stille coupling are Pd(PPh$_3$)$_4$, PdCl$_2$(PPh$_3$)$_2$, Pd(OAc)$_2$, tris(dibenzylideneacetone)dipalladium(0), tris(dibenzylideneacetone)dipalladium(0) chloroform complex, bis(dibenzylideneacetone)palladium(0), etc.

In order to accelerate the reaction, these palladium catalysts may be added with tetra-n-butylammonium chloride, tetra-n-butylammonium bromide, tetra-n-butylammonium iodide, etc., if necessary. Furthermore, polymerization inhibitors such as 2,6-di-tert-butyl-4-methylphenol (BHT), etc. may also be added to inhibit the formation of by-products.

Specific examples of the solvents used in the reaction are benzene, toluene, xylene, N,N-dimethylformamide, tetrahydrofuran, diethyl ether, t-butyl methyl ether, 1,4-dioxane, etc. These solvents may be appropriately chosen and used alone or as a solvent mixture thereof.

The reaction temperature and reaction time are not particularly limited and are, e.g., at 60° C. to 120° C. for an hour to 24 hours, preferably, at 80° C. to 110° C. for an hour to 12 hours, and more preferably, at 100° C. to 110° C. for an hour to 2 hours.

3. Method for Producing the Calcium-Binding Photoprotein

The calcium-binding photoprotein of the present invention can be produced or regenerated by contacting the compound represented by general formula (II) (the v-coelenterazine compound of the present invention) with an apoprotein of the calcium-binding photoprotein to give the calcium-binding photoprotein.

As used herein, the term "contact" means that the v-coelenterazine compound and an apoprotein of the calcium-binding photoprotein are allowed to be present in the same reaction system, and includes, for example, the states that an apoprotein of the calcium-binding photoprotein is added to a container charged with the v-coelenterazine compound, the v-coelenterazine compound is added to a container charged with an apoprotein of the calcium-binding photoprotein, the v-coelenterazine compound is mixed with an apoprotein of the calcium-binding photoprotein, and the like. In one embodiment of the present invention, the contact is effected at a low temperature in the presence of a reducing agent (e.g., mercaptoethanol, dithiothreitol, etc.) and oxygen. More specifically, the photoprotein of the present invention can be produced or regenerated by the methods described in, e.g., Shimomura, O. et al., *Biochem. J*, 251, 405-410 (1988), Shimomura, O. et al., *Biochem. J.*, 261, 913-920 (1989), etc. The calcium-binding photoprotein of the present invention exists in the state that a peroxide of the v-coelenterazine compound produced from the v-coelenterazine compound and molecular oxygen and the apoprotein form a complex in the presence of oxygen. When calcium ions bind to the complex described above, the complex emits light to generate the v-coelenteramide compound as the oxide of the v-coelenterazine compound and carbon dioxide. The complex described above is sometimes referred to as the "photoprotein of the present invention."

Examples of the apoprotein used to produce the photoprotein of the present invention include apoaequorin, apoclytin-I, apoclytin-II, apobelin, apomitrocomin, apomineopsin, apobervoin, and the like. In some embodiments of the present invention, the apoprotein is apoaequorin, apobelin, apoclytin-I, apoclytin-II, mitrocomin, etc., e.g., apoaequorin. These apoproteins may be obtained from natural sources or genetically engineered. Furthermore, the amino acid sequence may also be mutated from the native sequence by gene recombination technology, as long as the apoproteins are capable of producing the calcium-binding photoprotein.

The nucleotide sequences and amino acid sequences of the apoproteins of photoproteins obtained from the nature (native apoproteins) are as follows. The nucleotide sequence and amino acid sequence of native apoaequorin are shown by SEQ ID NO: 1 and SEQ ID NO: 2, respectively. The nucleotide sequence and amino acid sequence of native apoclytin-I are shown by SEQ ID NO: 3 and SEQ ID NO: 4, respectively. The nucleotide sequence and amino acid sequence of native apoclytin-II are shown by SEQ ID NO: 5 and SEQ ID NO: 6, respectively. The nucleotide sequence and amino acid sequence of native apomitrocomin are shown by SEQ ID NO: 7 and SEQ ID NO: 8, respectively. The nucleotide sequence and amino acid sequence of native apobelin are shown by SEQ ID NO: 9 and SEQ ID NO: 10, respectively. The nucleotide sequence and amino acid sequence of native apobervoin are shown by SEQ ID NO: 11 and SEQ ID NO: 12, respectively.

The apoprotein mutated by recombinant technology is, for example, a protein selected from the group consisting of (a) to (c) below:

(a) a protein comprising the amino acid sequence of native apoprotein in which 1 or more amino acids are deleted, substituted, inserted and/or added, and having the activity or function of the apoprotein of the calcium-binding photoprotein;

(b) a protein comprising an amino acid sequence which has 90% or more homology to the amino acid sequence of native apoprotein, and having the activity or function of the apoprotein of the calcium-binding photoprotein; and, (c) a protein comprising an amino acid sequence encoded by a polynucleotide that hybridizes under stringent conditions to a polynucleotide comprising a nucleotide sequence complementary to the nucleotide sequence of native apoprotein, and having the activity or function of the apoprotein of the calcium-binding photoprotein.

Examples of the "native apoprotein" described above are apoaequorin, apoclytin-I, apoclytin-II, apobelin, apomitrocomin, apomineopsin, apobervoin, etc. In an embodiment of the present invention, the apoprotein is apoaequorin, apobelin, apoclytin-I, apoclytin-II, apobelin, apomitrocomin, etc., preferably apoaequorin. The amino acid sequences and nucleotide sequences of these native apoproteins are the same as described above.

The term "activity or function of the apoprotein of the calcium-binding photoprotein" described above is used to mean, for example, the activity or function of the apoprotein which binds to a peroxide of the v-coelenterazine compound to produce the calcium-binding photoprotein. "The protein binds to a peroxide of the v-coelenterazine compound to produce the calcium-binding photoprotein" specifically means not only (1) that the protein binds to the peroxide of v-coelenterazine compound to produce the photoprotein, but also (2) that the protein is brought in contact with the v-coelenterazine compound in the presence of oxygen to produce the photoprotein (complex) containing the protein and a peroxide of the v-coelenterazine compound. As used herein, the term "contact" means that the protein and the v-coelenterazine compound are allowed to be present in the same reaction system, and includes, for example, addition of the protein to a container charged with the v-coelenterazine compound, addition of the v-coelenterazine compound to a container charged with the protein, mixing of the protein with the v-coelenterazine compound, and the like.

The "v-coelenterazine compound" refers to v-coelenterazine and as in v-coelenterazine, a compound capable of constituting as the apoprotein the calcium-binding photoprotein such as aequorin, etc. (v-coelenterazine analogue), specifically, cf3-v-coelenterazine.

The range of "1 or more" in "the amino acid sequence in which 1 or more amino acids are deleted, substituted, inserted and/or added" described above is, for example, 1 to 20, 1 to 15, 1 to 10, 1 to 9, 1 to 8, 1 to 7, 1 to 6 (1 to several), 1 to 5, 1 to 4, 1 to 3, 1 to 2, and 1. In general, the less the number of the amino acids deleted, substituted, inserted or added, the more preferable. In the deletion, substitution, insertion and addition of the amino acid residues described above, two or more may occur concurrently. Such regions can be acquired by using site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)", "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

The range of "90% or more" in the "amino acid sequence which has 90% or more homology" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. It is generally preferred for the numerical value indicating the degree of homology to be higher. The homology between amino acid sequences or nucleotide sequences can be determined using a sequencing program such as BLAST (see, e.g., Altzshul S. F. et al., J. Mol. Biol., 215, 403 (1990), etc.) or the like. When BLAST is used, the default parameters for the respective programs are used.

The "polynucleotide that hybridizes under stringent conditions" described above refers to a polynucleotide (e.g., DNA) which is obtained by, for example, colony hybridization, plaque hybridization, Southern hybridization, etc., using as a probe all or part of a polynucleotide comprising a nucleotide sequence complementary to the nucleotide sequence of native apoprotein or a polynucleotide encoding the amino acid sequence of native apoprotein. Specific examples include a polynucleotide which can be identified by performing hybridization at 65° C. in the presence of 0.7 to 1.0 mol/L NaCl using a filter on which the polynucleotide from a colony or plaque is immobilized, then washing the filter under 65° C. conditions with an SSC (saline-sodium citrate) solution having a concentration of 0.1 to 2 times (a 1×SSC solution is composed of 150 mmol/L of sodium chloride and 15 mmol/L of sodium citrate).

Hybridization may be performed in accordance with modifications of the methods described in textbooks of experiment, e.g., Sambrook J. et al., Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

As used herein, the term "stringent conditions" may refer to less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., DNA) of higher homology is expected to be obtained efficiently at higher temperatures, although multiple factors are involved in hybridization stringency, including temperature, probe concentration, probe length, ionic strength, time and base concentration; those skilled in the art may appropriately select these factors to realize a similar stringency.

When a commercially available kit is used for the hybridization, for example, AlkPhos Direct Labeling Reagents (manufactured by Amersham Pharmacia) can be used. According to the protocol attached to the kit in this case, incubation with a labeled probe is performed overnight, the membrane is then washed with a primary wash buffer containing 0.1% (w/v) SDS at 55° C., and finally the hybridized DNA can be detected.

Other hybridizable polynucleotides include, as calculated by a sequencing program such as BLAST or the like using the default parameters, DNAs having homology of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the amino acid sequence of the apoprotein. The homology of an amino acid sequence or a nucleotide sequence can be determined using the method described hereinabove.

Examples of the recombinant apoprotein which can be used in the present invention include recombinant aequorin described in Shimomura, O. and Inouye, S. Protein Express. Purif (1999) 16: 91-95, recombinant clytin-I described in Inouye, S. and Sahara, Y. Protein Express. Purif (2007) 53: 384-389, recombinant clytin-II described in Inouye, S. J. Biochem. (2008) 143: 711-717, and the like.

The calcium-binding photoprotein thus produced may be further purified. Purification of the calcium-binding photoprotein can be performed in a conventional manner of separation/purification. The separation/purification includes, for example, precipitation with ammonium sulfate, gel filtration chromatography, ion exchange chromatography, affinity chromatography, reversed phase high performance liquid chromatography, dialysis, ultrafiltration, etc., alone or in an appropriate combination of these techniques.

4. Use of v-Coelenterazine Compound of the Invention or Photoprotein of the Invention (1) Use as Luminescence Substrate The v-coelenterazine compound in some embodiments of the present invention emits light by the action of an emission-catalyzing enzyme and can be used as a luminescence substrate. Therefore, the present invention provides a method for emitting light which comprises contacting the v-coelenterazine compound of the present invention with an emission-catalyzing enzyme. As used herein, the term "contact" means that the v-coelenterazine compound of the present invention and an emission-catalyzing enzyme are allowed to be present in the same reaction system, and includes, for example, the states that the emission-catalyzing enzyme is added to a container charged with the v-coelenterazine compound, the v-coelenterazine compound is added to a container charged with the emission-catalyzing enzyme, the v-coelenterazine compound is mixed with the emission-catalyzing enzyme, and the like.

The emission-catalyzing enzyme used in the method of the present invention for emitting light is, for example, a luciferase derived from *Oplophorus* sp., e.g., *Oplophorus grachlorostris* (*Oplophorus* luciferase), a luciferase derived from *Gaussia* sp., e.g., *Gaussia princeps* (*Gaussia* luciferase), a luciferase derived from *Renilla* sp., e.g., *Renilla reniformis*, or *Renilla muelleri* (*Renilla* luciferase), a luciferase derived from *Pleuromamma* sp. (*Pleuromamma* luciferase) or a luciferase derived from *Metridia longa* (*Metridia* luciferase).

The emission-catalyzing enzyme used for the method of the present invention for emitting light may be mutants of these luciferases. Examples of the mutants include mutants of *Renilla* luciferase described in Loening et al. Protein Eng. Des. Sel. (2006) 19, 391-400, mutants of *Renilla* luciferase described in Loening et al. Nature methods (2007) 4, 641-643, mutants of *Renilla* luciferase described in Woo et al. Protein Sci. (2008) 17, 725-735, etc.

These emission-catalyzing enzymes can be prepared by the method described in, e.g., Shimomura et al. (1988) Biochem. J. 251, 405-410, Shimomura et al. (1989) Biochem. J. 261, 913-920, or Shimomura et al. (1990) Biochem. J. 270, 309-312, or modifications thereof. Alternatively, various types of the enzymes are commercially available from JNC Corporation (former Chisso Corporation), Wako Pure Chemical, Promega Inc., etc. and these enzymes commercially available may also be employed for the method of the present invention for emitting light.

Among the *Renilla* luciferase, the nucleotide sequence and amino acid sequence of *Renilla reniformis*-derived luciferase are shown by SEQ ID NO: 13 and SEQ ID NO: 14, respectively. The nucleotide sequence and amino acid sequence of *Oplophorus grachlorostris*-derived luciferase among the *Oplophorus* luciferase are shown by SEQ ID NO: 15 and SEQ ID NO: 16, respectively. The nucleotide sequence and amino acid sequence of *Gaussia princeps*-derived luciferase in the *Gaussia* luciferase are shown by SEQ ID NO: 17 and SEQ ID NO: 18, respectively.

The nucleotide sequence and amino acid sequence of *Renilla* luciferase mutant described in Inouye & Shimomura, Biochem. Biophys. Res. Commun., 233 (1997) 349-353 are shown by SEQ ID NO: 19 and SEQ ID NO: 20, respectively.

In one embodiment of the present invention, *Renilla reniformis*-derived luciferase, e.g., a protein comprising a polypeptide consisting of the amino acid sequence of SEQ ID NO: 14 is used as the emission-catalyzing enzyme.

In another embodiment of the present invention, a mutant of *Renilla* luciferase, e.g., a protein comprising a polypeptide consisting of the amino acid sequence of SEQ ID NO: 20 is used as the emission-catalyzing enzyme. In some embodiments of the present invention, the maximum emission wavelength can be shifted toward the longer wavelength side relative to *Renilla reniformis*-derived luciferase by using the mutant of *Renilla* luciferase as the emission-catalyzing enzyme.

Light emits by contacting these emission-catalyzing enzymes with the v-coelenterazine compound in some embodiments of the present invention. The emission time is usually 0.01 to an hour. However, the emission time may be prolonged or further shortened by selecting conditions.

(2) Detection or Quantification of Calcium Ions

The photoprotein of the present invention obtained as described above is a non-covalent complex of an apoprotein and a peroxide of the v-coelenterazine compound formed from the v-coelenterazine compound and molecular oxygen and is a photoprotein (holoprotein) that emits light by the action of calcium ions. Therefore, the photoprotein of the invention can be used for the detection or quantification of calcium ions.

The detection or quantification of calcium ions can be performed, for example, by adding a sample solution directly to a solution of the photoprotein and measuring the luminescence generated. Alternatively, calcium ions can also be detected or quantified by adding a solution of the photoprotein to a sample solution and measuring the luminescence generated. The photoprotein above may be formed by previously contacting an aqueous apoprotein solution with the v-coelenterazine compound of the present invention prior to its addition to the assay system for the detection or quantification of calcium ions and the resulting photoprotein may be provided for use. The photoprotein comprising an apoprotein and a peroxide of the v-coelenterazine compound may also be formed in the assay system by contacting the apoprotein with the v-coelenterazine compound. The photoprotein formed is a complex (photoprotein) of the apoprotein and the peroxide of the v-coelenterazine compound of the invention. The above complex (i.e., the photoprotein of the present invention) emits light dependently on the calcium ion concentration.

The detection or quantification of calcium ions can be performed by measuring the luminescence of the photoprotein of the invention through the action of calcium ions, using a luminometer. Luminometers which may be used include commercially available instruments, such as a Centro LB 960 (manufactured by Berthold, Inc.), etc. The calcium ion concentration can be quantitatively determined by preparing a luminescence standard curve for known calcium ion concentrations using the photoprotein.

The v-coelenterazine compound of the present invention may also be used for the detection of changes in the intracellular calcium ion concentration under the physiological conditions by preparing the photoprotein comprising an apoprotein and a peroxide of the v-coelenterazine compound and injecting the photoprotein directly into cells by means of microinjection, etc.

The v-coelenterazine compound of the present invention may also be used to produce the photoprotein, which is performed, in addition to the injection using techniques such as microinjection, by intracellularly expressing a gene for the apoprotein (a polynucleotide encoding the apoprotein) to produce the protein in the cells and adding the v-coelenterazine compound of the present invention to the resulting apoprotein from the external cells.

Using the photoprotein of the present invention thus introduced into cells or produced in cells, changes in the intracellular calcium ion concentration caused by external stimulation (e.g., stimulation with receptor-associated drugs, etc.) can also be determined.

(3) Use as Reporter Protein, etc. Utilizing Luminescence

The photoprotein of the present invention can also be used as a reporter protein to determine the transcription activity of a promoter, etc. A polynucleotide encoding an apoprotein is fused to a target promoter or other expression control sequence (e.g., an enhancer, etc.) to construct a vector. The vector described above is transfected to a host cell, and the v-coelenterazine compound of the present invention is brought in contact with the cell. By detecting the luminescence from the photoprotein of the present invention, the activity of the target promoter or other expression control sequence can be determined. As used herein, the term "contact" means that a host cell and the v-coelenterazine compound are allowed to be present in the same culture system/reaction system, and includes, for example, addition of the v-coelenterazine compound to a culture container charged with a host cell, mixing of a host cell with the v-coelenterazine compound, culture of a host cell in the presence of the v-coelenterazine compound, and the like.

The v-coelenterazine compound of the present invention can be used to determine the transcription activity of a promoter, etc. For example, a polynucleotide encoding the emission-catalyzing enzyme is fused to a target promoter or other expression control sequence (e.g., an enhancer, etc.) to construct a vector. The vector described above is transfected to a host cell, and the v-coelenterazine compound of the present invention is contacted with the cell. By detecting the luminescence from the v-coelenterazine compound of the present invention, the activity of the target promoter or other expression control sequence can be determined. As used herein, the term "contact" means that a host cell and the v-coelenterazine compound of the present invention are allowed to be present in the same culture system/reaction system, and includes, for example, addition of the v-coelenterazine compound to a culture container charged with a host cell, mixing of a host cell with the v-coelenterazine compound, culture of a host cell in the presence of the v-coelenterazine compound, and the like. The emission-catalyzing enzyme is described above and is at least one luciferase selected from the group consisting of *Renilla* luciferase, *Oplophorus* luciferase, *Gaussia* luciferase and mutants thereof, and preferably, *Renilla* luciferase mutants.

The present invention further provides a kit used for the measurement of transcription activity of a promoter, etc. In some embodiments of the present invention, the kit comprises the v-coelenterazine compound of the present invention and the emission-catalyzing enzyme. In another embodiment of the present invention, the kit comprises the photoprotein of the present invention and the coelenterazine compound. Reagent such as the coelenterazine compound, the emission-catalyzing enzyme, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

(4) Use as Detection Marker, etc. Utilizing Luminescence

The photoprotein of the present invention can be used as a marker for detection by luminescence. The detection marker of the present invention can be used to detect a target substance in, e.g., immunoassay, hybridization assay, etc. The photoprotein of the present invention can be used in the form bound to a target substance (protein, nucleic acid, etc.) in a conventional manner including chemical modification. Detection methods using such a detection marker can be performed in a conventional manner. The detection marker of the present invention can also be used to determine the distribution of a target substance by expressing the marker, e.g., as a fusion protein of the apoprotein and the target substance, then inserting the fusion protein into cells by means of microinjection or the like and contacting them with the v-coelenterazine compound of the present invention thereby to produce the photoprotein of the present invention. As used herein, the term "contact" means that cells and the v-coelenterazine compound of the present invention are allowed to be present in the same culture system/reaction system, and includes, for example, addition of the v-coelenterazine compound of the present invention to a culture container charged with cells, mixing of cells with the v-coelenterazine compound of the present invention, culture of host cells in the presence of the v-coelenterazine compound of the present invention, and the like.

The present invention further provides a method for detection of a target substance in, e.g., immunoassay, hybridization assay, etc., which comprises using the v-coelenterazine compound and the emission-catalyzing enzyme. In this case, the emission-catalyzing enzyme can be used in the form bound to the target substance (protein, nucleic acid, etc.) in a conventional manner, including chemical modification. Such a detection method using the detection marker can be performed in a conventional manner. The detection marker can also be used to determine the distribution of the target substance by expressing the marker, e.g., as a fusion protein of the emission-catalyzing enzyme and the target substance, then inserting the fusion protein into cells by means of microinjection or the like and contacting it with the v-coelenterazine compound of the present invention. As used herein, the term "contact" means that a cell and the v-coelenterazine compound of the present invention are allowed to be present in the same culture system/reaction system, and includes, for example, addition of the v-coelenterazine compound of the present invention to a culture container charged with a cell, mixing of a cell with the v-coelenterazine compound of the present invention, culture of a host cell in the presence of the v-coelenterazine compound of the present invention, and the like. The emission-catalyzing enzyme is the same as described above and is, for example, at least one luciferase selected from the group consisting of *Renilla* luciferase, *Oplophorus* luciferase and *Gaussia* luciferase.

The distribution of these target substances, etc. can be determined by a method for detection such as luminescence imaging, etc. The apoprotein may also be used after its expression in cells, in addition to the insertion into cells by means of microinjection, etc.

The present invention further provides a kit used for the detection of a target substance in an immunoassay, hybridization assay, etc. The kit in some embodiments of the present invention comprises the photoprotein of the present invention and the coelenterazine compound. The kit in another embodiment of the present invention comprises the v-coelenterazine compound of the present invention and the emission-catalyzing enzyme. Reagent such as the coelenterazine compound, the emission-catalyzing enzyme, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

(5) Material for Amusement Supplies

The complex (photoprotein of the present invention) comprising the apoprotein and a peroxide of the v-coelenterazine compound of the present invention emits light only by binding to a trace of calcium ions. The photoprotein of the present invention can thus be preferably used as a luminescence material for amusement supplies. Examples of such amusement supplies are luminescent soap bubbles, luminescent ice, luminescent candies, luminescent color paints, etc. The amusement supplies of the present invention can be prepared in a conventional manner.

(6) Bioluminescence Resonance Energy Transfer (BRET) Method

In some embodiments of the present invention, the v-coelenterazine compound emits light by the action of the emission-catalyzing enzyme as described above, and can be used for analysis methods including an analysis of physiological functions, an analysis of (or assay for) enzyme activities, etc., based on the principle of intermolecular interaction by the bioluminescence resonance energy transfer (BRET) method. The photoprotein of the present invention can also be used for analyses including an analysis of biological functions, an assay for enzyme activities, etc., based on the principle of intermolecular interaction by the bioluminescence resonance energy transfer (BRET) method.

For example, using the v-coelenterazine compound and the emission-catalyzing enzyme in some embodiments of the present invention as donor proteins and as an acceptor protein an organic compound or a fluorescent protein, the interaction between the proteins can be detected by generating bioluminescence resonance energy transfer (BRET) between them. As used herein, the emission-catalyzing enzyme is the same as given before and is, for example, at least one luciferase selected from the group consisting of *Renilla* luciferase, *Oplophorus* luciferase and *Gaussia* luciferase.

Alternatively, using the photoprotein of the invention as a donor protein and an organic compound or a fluorescent protein as an acceptor protein, the interaction between the proteins can be detected by generating bioluminescence resonance energy transfer (BRET) between them. In a certain embodiment of the present invention, the organic compound used as an acceptor protein is Hoechist 3342, Indo-1, DAPI, etc. In another embodiment of the present invention, the fluorescent protein used as an acceptor protein is a green fluorescent protein (GFP), a blue fluorescent protein (BFP), a mutant GFP fluorescent protein, phycobilin, etc. In a preferred embodiment of the present invention, the physiological functions to be analyzed include an orphan receptor (in particular, G-protein conjugated receptor), apoptosis, transcription regulation, etc. by gene expression. Still in a preferred embodiment of the present invention, the enzyme to be analyzed is protease, esterase, kinase, etc.

Analysis of the physiological functions by the BRET method may be performed by known methods, for example, by modifications of the methods described in Biochem. J. 2005, 385, 625-637, Expert Opin. Ther. Targets, 2007 11: 541-556, etc. Assay for the enzyme activities may also be performed by known methods, for example, by modifications of the methods described in Nat. Methods 2006, 3:165-174, Biotechnol. J. 2008, 3: 311-324, etc.

The present invention further provides a kit used for the analysis methods described above. The kit comprises the v-coelenterazine compound of the present invention, the emission-catalyzing enzyme and the organic compound and/or the fluorescent protein. Reagents such as the v-coelenterazine compounds, the emission-catalyzing enzymes, organic compounds, fluorescent proteins, etc. may be dissolved in a suitable solvent and prepared to be suitable for storage. The solvent which may be used is at least one selected from the group consisting of water, ethanol, various buffer solutions, and the like. The kit may additionally comprise, if necessary, at least one selected from the group consisting of a container designed therefor, other necessary accessories and an instruction manual, and the like.

All literatures and publications mentioned in this specification are herein incorporated in their entirety by reference into the specification, irrespective of their purposes. The disclosure of the specification, the claims, abstract and drawings of Japanese Application JP2011-050487 filed on Mar. 8, 2011, based upon which the present application claims the benefit of priority, are entirely incorporated herein by reference.

The objects, characteristics and advantages of the present invention as well as the idea thereof are apparent to those skilled in the art from the descriptions given herein, and those skilled in the art can easily implement the present invention. It is to be understood that the best mode to carry out the invention and specific examples are to be taken as preferred embodiments of the present invention. These descriptions are only for illustrative and explanatory purposes and are not intended to restrict the invention thereto. It is apparent to those skilled in the art that various modifications may be made based on the descriptions given herein within the intent and scope of the present invention disclosed herein.

EXAMPLES

Hereinafter, the present invention will be illustrated more specifically with reference to SYNTHESIS EXAMPLES and EXAMPLES, but it should be understood that the invention is not deemed to be limited to these SYNTHESIS EXAMPLES and EXAMPLES.

SYNTHESIS EXAMPLES

Overview
    The process for producing the v-coelenterazine compound illustratively shown in these SYNTHESIS EXAMPLES is a highly flexible and highly efficient process which is applicable to the production of various v-coelenterazine analogues.

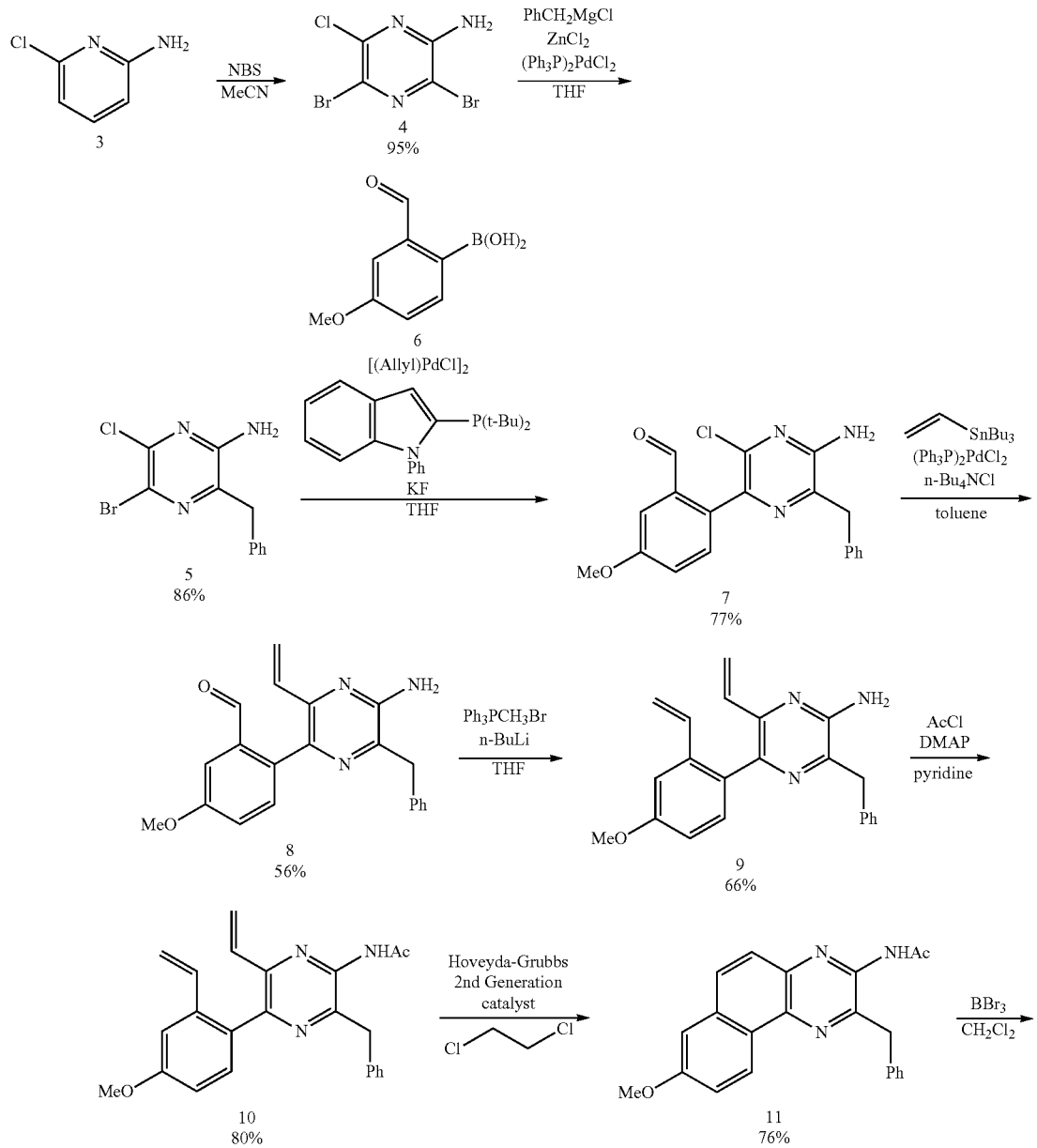

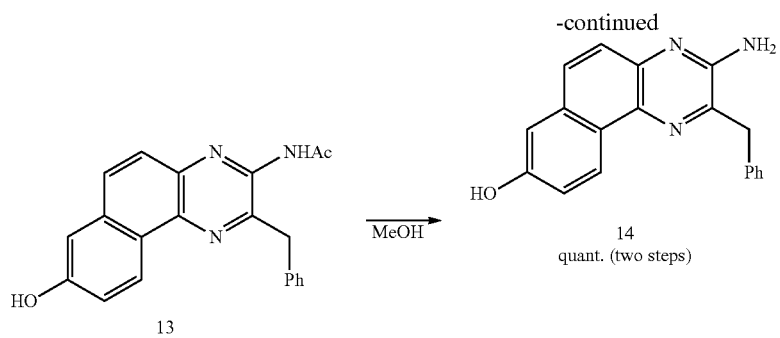

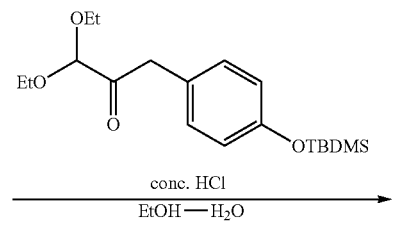

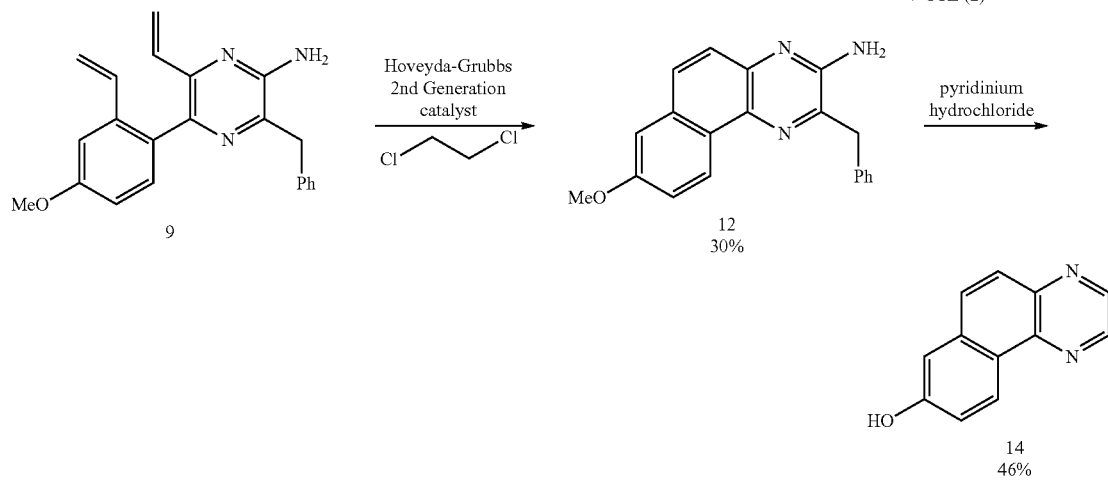

More specifically, in these SYNTHESIS EXAMPLES, commercially available 2-chloro-6-aminopyrazine 3 was first dibrominated to synthesize known Compound 4 (WO 2003/059893). The compound was subjected to the Negishi coupling with benzyl zinc reagent to introduce benzyl into Compound 4, whereby Compound 5 could be obtained. Next, the Suzuki-Miyaura coupling was performed between Compound 5 and boronic acid 6 so that Compound 5 was arylated at the 5-position selectively to give Compound 7. Then, the 6-position of Compound 7 was vinylated through the Stille coupling with vinyl tin to give Compound 8 successfully. It is considered that the respective substituents could be introduced with high position selectivity by the effect of unprotected amino group in these 3 types of the coupling reactions.

The formyl group of Compound 8 obtained was further methylated to give Compound 9. After the amino group in Compound 9 was protected with acetyl, the ring-closing metathesis reaction was performed using a Hoveyda-Grubbs second generation catalyst, whereby tricyclic aromatic Compound 11 could be efficiently obtained. In this case, though the yield was low, the ring-closing metathesis reaction could proceed to give the corresponding cyclic product 12 from Compound 9 with the amino being unprotected. However, it was found that the ring closing reaction proceeded more efficiently with an acyl-protected compound.

Subsequently, the methyl group in Compound 11 was removed by boron tribromide. The resulting Compound 13 was heated in methanol in the presence of a small quantity of sodium hydrogencarbonate for deprotection of acetyl to give v-coelenteramine 4. For removal of the methyl group in Compound 12 wherein the amino group is not protected with acetyl group, boron tribromide could not be used but by heating with pyridine hydrochloride, v-coelenteramine 14 could be obtained while the yield was low.

Finally, v-coelenteramine 14 was condensed and cyclized with the ketacetal 15. Thus, v-CTZ (2) could be synthesized.

This synthetic route is as short as 8 to 10 steps from the commercially available compound. In addition, the stability is expected to be improved by varying the substituent on the benzene ring of the ketacetal used in the final step, and a variety of v-CTZ analogues can be synthesized in a simple manner (cf., e.g., the equation below).

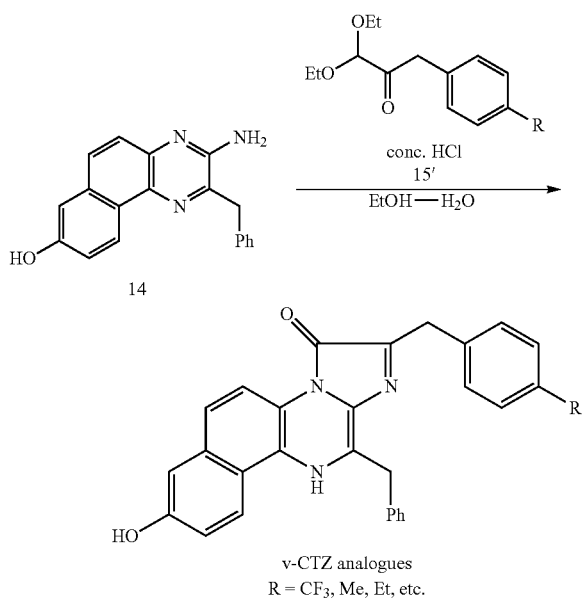

v-CTZ analogues
R = CF₃, Me, Et, etc.

In the future it is expected that v-CTZ compounds suitable for diverse applications including near-infra red luminescent imaging can be newly produced by using this process for synthesis.

Materials and Methods (1) Chromatography

Thin layer chromatography (TLC) for analysis was performed on a glass plate (MERCK 5715, silica gel 60 $F_{254}$) previously coated with silica gel. The spots were detected under a LTV lamp (254 nm or 365 nm) by adsorbing iodine, dipping in an aqueous anisaldehyde solution and charring on a hot plate.

For preparative flush column chromatography, silica gels (Kanto Chemical Co., Inc., 37563-85, silica gel 60 N (spherical, neutral), particle size 45-50 μm or Kanto Chemical Co., Inc., 37565-85, silica gel 60 N (spherical, neutral), particle size 63-210 μm) were used. For purification of the CTZ analogues, however, silica gels (Kanto Chemical Co., Inc., 37562-79, silica gel 60 N (spherical), particle size 40-50 μm or Kanto Chemical Co., Inc., 37558-79, silica gel 60 N (spherical), particle size 100-210 μm) were used.

(2) Nuclear Magnetic Resonance (NMR) Spectrum

¹H Nuclear magnetic resonance (NMR) spectrum (400 MHz) was determined on an AVANCE 400 or AVANCE 500 nuclear magnetic resonance apparatus manufactured by Bruker, Inc. Chemical shifts (δ) were expressed as values relative to the peaks from tetramethylsilane (($CH_3$)$_4$Si) (measured in $CDCl_3$; 0 ppm) or the peaks from non-deuterated solvent for analysis (measured in $CD_3OD$; 3.31 ppm; measured in DMSO-$d_6$; 2.49 ppm) as an internal standard. Abbreviations s, d and m used for the signal splitting patterns represent singlet, doublet and multiplet, respectively.

¹³C Nuclear magnetic resonance spectrum (100 MHz) was determined by a AVANCE 400 nuclear magnetic resonance apparatus manufactured by Bruker, Inc. Chemical shifts (δ) were expressed as values relative to the peaks from carbon in the solvent for analysis (measured in $CDCl_3$; 77.0 ppm, measured in $CD_3OD$; 49.0 ppm) as an internal standard.

(3) Infrared Absorption (IR) Spectrum

IR spectra were determined by the diffuse reflection method using a SHIMAZU IR Prestige-21 spectrophotometer equipped with DRS-8000, manufactured by Shimadzu Corporation.

(4) Mass Spectrometry

High resolution mass spectrometry (HRMS) was performed by the electrospray ionization method (ESI) with a Bruker micrOTOF manufactured by Bruker, Inc.

(5) Chemical Reagent

The reagents were used without further treatment unless otherwise indicated.

The solvents for the reactions, extractions and chromatography were acetonitrile, ethyl acetate, n-hexane, anhydrous tetrahydrofuran (THF), toluene, anhydrous pyridine, 1,2-dichloroethane, anhydrous dichloromethane, methanol and ethanol, all commercially available, and used without further treatment. Unless otherwise indicated, mixing ratios in the solvent mixtures used are based on "v/v."

The reaction reagents below were used. 2-Amino-6-chloropyrazine (Cat. No. 1650) purchased from Matrix Scientific, N-bromosuccinimide (Cat. No. 025-07235), 2-formyl-4-methoxyphenylboronic acid (Cat. No. 328-99903), potassium fluoride (Cat. No. 169-03765), tetra-n-butylammonium chloride (Cat. No. T0054), methyltriphenylphosphonium bromide (Cat. No. 138-11961), 4-(dimethylamino)pyridine (Cat. No. 042-19212), acetyl chloride (Cat. No. 011-0053), conc. hydrochloric acid (Cat. No. 080-01066) and pyridinium hydrochloride (Cat. No. 163-11931) purchased from Wako Pure Chemical Co., Ltd., zinc chloride (1.0 M in diethyl ether) (Cat. No. 276839), benzyl magnesium chloride (2.0 M in THF) (Cat. No. 225916), dichlorobis(triphenylphosphine) palladium(II) (Cat. No. 412740), 2-(di-tert-butylphosphino)-1-phenylindole (Cat. No. 672343), tributyl(vinyl)tin (Cat. No. 271438), Hoveyda-Grubbs second generation catalyst (Cat. No. 569755) and boron tribromide (1:0 M in dichloromethane) (Cat. No. 211222) purchased from Aldrich, Inc., allyl palladium(II) chloride dimer (Cat. No. A1479) purchased from Tokyo Chemical Industry Co., Ltd., n-butyl lithium (1.65 M in n-hexane (Cat. No. 04937-25) purchased from Kanto Chemical Co., Inc.; were used in the reactions without further treatment.

SYNTHESIS EXAMPLE 1

2-Amino-3,5-dibromo-6-chloropyrazine (4)

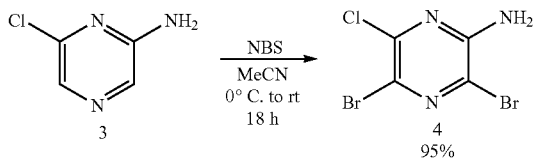

To a solution of 2-amino-6-chloropyrazine (3) (8.00 g, 61.8 mmol) in acetonitrile (80 mL) was gradually added N-bromosuccinimide (NBS) (27.5 g, 155 mmol) at 0° C. After elevating to room temperature, the mixture was stirred overnight (18 hours). To the mixture was added water and the product was extracted with diethyl ether (×3). The combined organic extract was washed successively with water (×1) and brine (×1), followed by drying over anhydrous sodium sulfate. After filtration and concentration under reduced pressure, the residue was purified by silica gel flash column chromatography (n-hexane/ethyl acetate=3/1) to give 2-amino-3,5-dibromo-6-chloropyrazine (4) (16.8 g, 58.5 mmol, 94.7%) as a yellow solid. TLC $R_f$=0.31 (n-hexane/ethyl acetate=4/1);

$^1$H NMR (500 MHz, CDCl$_3$) δ 5.14 (s, 2H); $^{13}$C NMR (126 MHz, CDCl$_3$) δ 120.7, 122.0, 146.1, 151.0.

SYNTHESIS EXAMPLE 2

2-Amino-3-benzyl-5-bromo-6-chloropyrazine (5)

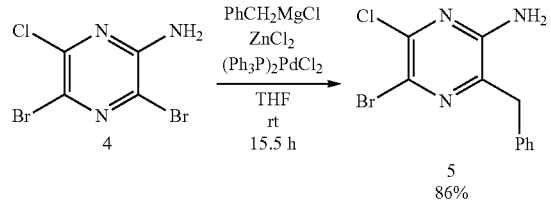 [SMILES: Nc1nc(Cl)c(Br)nc1Br ; Nc1nc(Cl)c(Br)nc1Cc1ccccc1]

Under an argon atmosphere, to anhydrous THF (40 mL) was added zinc chloride (1.0 M in diethyl ether) (23.7 mL, 23.7 mmol), and to the mixture was added benzyl magnesium chloride (2.0 M in THF) (10.4 mL, 20.8 mmol). After stirring at room temperature for 30 minutes, to the mixture were successively added dichlorobis(triphenylphosphine)palladium(II) (488 mg, 695 μmol) and 2-amino-3,5-dibromo-6-chloropyrazine (4) (4.00 g, 13.9 mmol) at room temperature. The mixture was stirred overnight (15 hours and a half) at room temperature as it was. After to the mixture was added water, the product was extracted with ethyl acetate (×3). The combined organic extract was washed successively with water (×1) and brine (×1), followed by drying over anhydrous sodium sulfate. After filtration and concentration under reduced pressure, the residue was purified by silica gel flash column chromatography (n-hexane/ethyl acetate=5/1) to give 2-amino-3-benzyl-5-bromo-6-chloropyrazine (5) (3.64 g, 12.2 mmol, 87.6%) as a yellow solid. TLC R$_f$=0.25 (n-hexane/ethyl acetate=4/1); $^1$H NMR (500 MHz, CDCl$_3$) δ 4.08 (s, 2H), 4.50 (s, 2H), 7.19-7.24 (m, 2H), 7.27-7.37 (m, 3H); $^{13}$C NMR (126 MHz, CDCl$_3$) δ 40.1, 123.8, 127.5, 128.4, 129.3, 135.3, 139.5, 144.9, 151.3.

SYNTHESIS EXAMPLE 3

2-(5-Amino-6-benzyl-3-chloropyrazin-2-yl)-5-methoxybenzaldehyde (7)

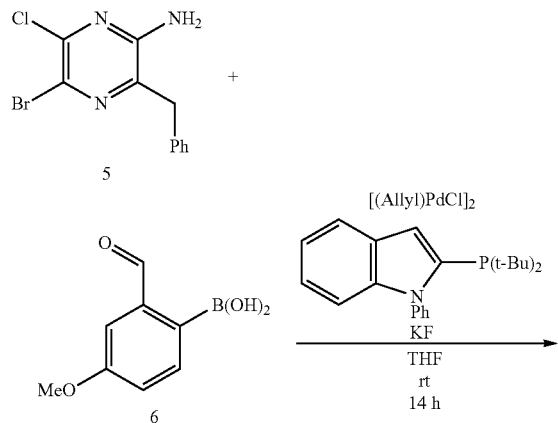

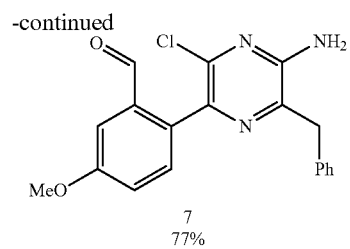

Under an argon atmosphere, to a solution of allylpalladium (II) chloride dimer (160 mg, 437 μmol) in anhydrous THF (30 mL) was added 2-(di-tert-butylphosphino)-1-phenylindole (295 mg, 874 μmol) at room temperature, followed by stirring at room temperature for 10 minutes. Subsequently, to the mixture were successively added 2-amino-3-benzyl-5-bromo-6-chloropyrazine (5) (2.60 g, 8.74 mmol), 2-formyl-4-methoxyphenylboronic acid (6) (3.14 g, 17.4 mmol), potassium fluoride (2.60 g, 44.8 mmol) and water (160 μL, 8.88 mmol) at room temperature. The mixture was stirred overnight (14 hours) at room temperature without further treatment. After to this was added water, the product was extracted with ethyl acetate (×3). The combined organic extract was washed successively with water (×1) and brine (×1), and dried over anhydrous sodium sulfate. After filtration and concentration under reduced pressure, the residue was purified by silica gel flash column chromatography (n-hexane/ethyl acetate=3/1) to give 2-(5-amino-6-benzyl-3-chloropyrazin-2-yl)-5-methoxybenzaldehyde (7) (2.37 g, 6.70 mmol, 76.9%) as a reddish brown solid. TLC R$_f$=0.27 (n-hexane/ethyl acetate=3/1); $^1$H NMR (500 MHz, CDCl$_3$) δ 3.92 (s, 3H), 4.13 (s, 2H), 4.66 (s, 2H), 7.21-7.25 (m, 3H), 7.27-7.31 (m, 1H), 7.32-7.37 (m, 2H), 7.51-7.55 (m, 2H), 9.92 (s, 1H).; $^{13}$C NMR (126 MHz, CDCl$_3$) δ 40.4, 55.7, 111.2, 120.7, 127.4, 128.4 (2C), 129.2 (2C), 132.5, 132.7, 135.7, 135.8, 137.8, 139.1, 144.1, 151.5, 160.0, 191.0.

SYNTHESIS EXAMPLE 4

2-(5-Amino-6-benzyl-3-vinylpyrazin-2-yl)-5-methoxybenzaldehyde (8)

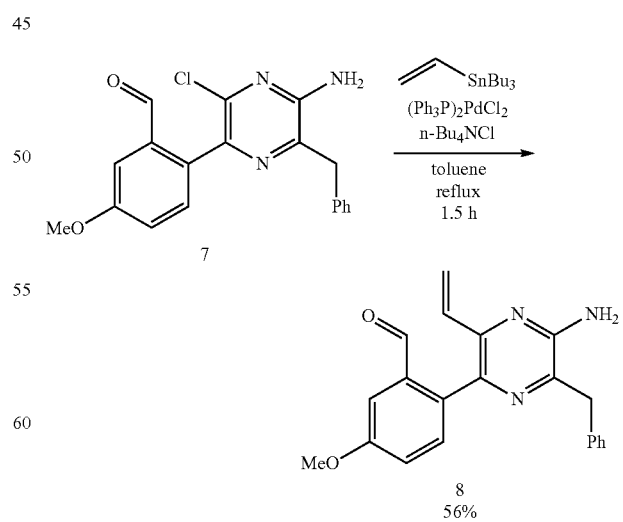

Under an argon atmosphere, to a solution of 2-(5-amino-6-benzyl-3-chloropyrazin-2-yl)-5-methoxybenzaldehyde (7)

(2.28 g, 6.44 mmol) in deaerated toluene (30 mL) were successively added dichlorobis(triphenylphosphine)palladium (II) (226 mg, 322 mol), tributyl(vinyl)tin (3.75 mL, 12.8 mmol) and tetra-n-butylammonium chloride (3.50 g, 12.6 mmol) at room temperature. The mixture was heated to reflux for 1.5 hours (oil bath temperature at 110° C.). After cooling to room temperature, to the mixture was added water and the product was extracted with ethyl acetate (×3). The combined organic extract was washed successively with water (×1) and brine (×1) followed by drying over anhydrous sodium sulfate. After filtration and concentration under reduced pressure, the residue was purified by silica gel flash column chromatography (silica gel mixed with 10 wt % potassium fluoride, n-hexane/ethyl acetate=3/1) to give 2-(5-amino-6-benzyl-3-vinylpyrazin-2-yl)-5-methoxybenzaldehyde (8) (1.24 g, 3.59 mmol, 55.5%) as a reddish brown oily substance. TLC $R_f$=0.27 (n-hexane/ethyl acetate=3/1); $^1$H NMR (500 MHz, CDCl$_3$) δ 3.92 (s, 3H), 4.15 (s, 2H), 4.50 (s, 2H), 5.39 (dd, 1H, J=2.0, 11.0 Hz), 6.33 (dd, 1H, J=2.0, 17.0 Hz), 6.57 (dd, 1H, J=11.0, 17.0 Hz), 7.20-7.28 (m, 4H), 7.30-7.36 (m, 2H), 7.41 (d, 1H, J=8.5 Hz), 7.55 (d, 1H, J=3.0 Hz), 9.88 (s, 1H); $^{13}$C NMR (126 MHz, CDCl$_3$) δ 41.0, 55.7, 110.6, 120.5, 121.0, 127.2, 128.5 (2C), 129.1 (2C), 132.3, 132.9, 134.4, 136.1, 136.5, 138.7, 140.2, 145.2, 151.5, 159.8, 191.5.

SYNTHESIS EXAMPLE 5

2-Amino-3-benzyl-5-(4-methoxy-2-vinylphenyl)-6-vinylpyrazine (9)

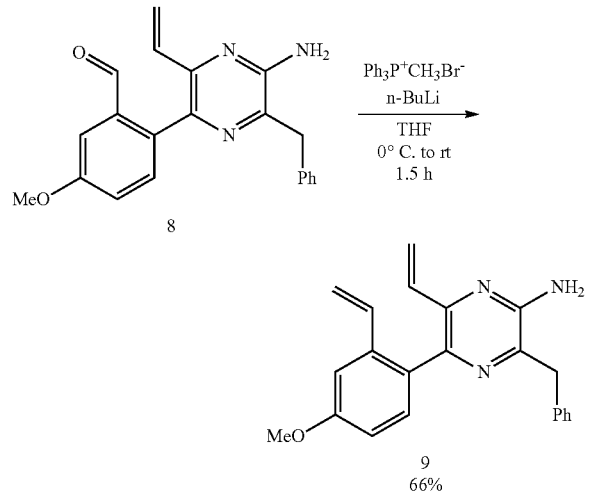

Under an argon atmosphere, to a suspension of methyltriphenylphosphonium bromide (1.29 g, 3.61 mmol) in anhydrous THF (5 mL) was gradually dropwise added n-butyl lithium (1.65 M in n-hexane) (1.70 mL, 2.81 mmol) at 0° C. The mixture was stirred at 0° C. for 15 minutes as it was. To the mixture was added 2-(5-amino-6-benzyl-3-vinylpyrazin-2-yl)-5-methoxybenzaldehyde (8) (871 mg, 2.52 mmol) at 0° C. After elevating to room temperature, stirring was continued for 1.5 hours. After to this was added water, the product was extracted with ethyl acetate (×3). The combined organic extract was washed successively with water (×1) and brine (×1), followed by drying over anhydrous sodium sulfate. After filtration and concentration under reduced pressure, the residue was purified by silica gel flash column chromatography (n-hexane/ethyl acetate=3/1) to give 2-amino-3-benzyl-5-(4-methoxy-2-vinylphenyl)-6-vinylpyrazine (9) (570 mg, 1.66 mmol, 65.8%) as a white solid. TLC $R_f$=0.37 (n-hexane/ethyl acetate=3/1); $^1$H NMR (500 MHz, CDCl$_3$) δ 3.88 (s, 3H), 4.16 (s, 2H), 4.39 (s, 2H), 5.18 (dd, 1H, J=1.0, 10.5 Hz), 5.30 (dd, 1H, J=2.0, 10.5 Hz), 5.67 (dd, 1H, J=1.0, 17.5 Hz), 6.25 (dd, 1H, J=2.0, 17.5 Hz), 6.47 (dd, 1H, J=10.5, 17.5 Hz), 6.50 (dd, 1H, J=10.5, 17.5 Hz), 6.90 (dd, 1H, J=2.5, 8.0 Hz), 7.20-7.26 (m, 5H), 7.29-7.35 (m, 2H); $^{13}$C MR. (126 MHz, CDCl$_3$) δ 41.2, 55.6, 110.5, 113.8, 115.4, 119.3, 127.2, 128.7 (2C), 129.2 (2C), 129.8, 132.1, 133.0, 135.1, 137.0, 138.3, 140.3, 141.9, 144.8, 151.4, 159.8.

SYNTHESIS EXAMPLE 6

N-(3-Benzyl-5-(4-methoxy-2-vinylphenyl)-6-vinylpyrazin-2-yl)acetamide (10)

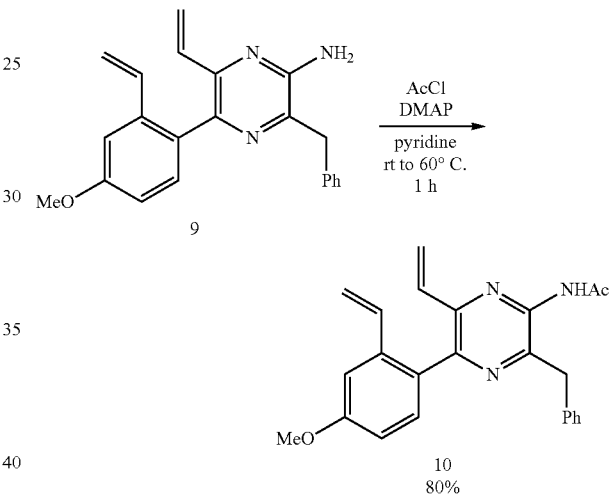

Under an argon atmosphere, to a solution of 2-amino-3-benzyl-5-(4-methoxy-2-vinylphenyl)-6-vinylpyrazine (9) (100 mg, 292 μmol) in anhydrous pyridine (20 mL) were successively added 4-(dimethylamino)pyridine (DMAP) (3.0 mg, 25 μmol) and acetyl chloride (65.0 μL, 911 μmol) at room temperature. The mixture was heated at 60° C. and stirred for an hour. After cooling to room temperature, to the mixture was added water and the product was extracted with ethyl acetate (×3). The combined organic extract was washed successively with water (×1) and brine (×1), followed by drying over anhydrous sodium sulfate. After filtration and concentration under reduced pressure, the residue was purified by silica gel flash column chromatography (n-hexane/ethyl acetate=3/1) to give N-(3-benzyl-5-(4-methoxy-2-vinylphenyl)-6-vinylpyrazin-2-yl)acetamide (10) (89.5 mg, 232 μmol, 79.7%) as a yellow solid. TLC $R_f$=0.17 (n-hexane/ethyl acetate=3/1); $^1$H NMR (400 MHz, CDCl$_3$) δ 2.33 (s, 3H), 3.89 (s, 3H), 4.28 (s, 2H), 5.19 (dd, 1H, J=1.0, 10.8 Hz), 5.39 (dd, 1H, J=2.0, 10.8 Hz), 5.66 (dd, 1H, J=1.0, 17.2 Hz), 6.30 (dd, 1H, J=2.0, 17.2 Hz), 6.45 (dd, 1H, J=10.8, 17.2 Hz), 6.52 (dd, 1H, J=10.8, 17.2 Hz), 6.94 (dd, 1H, J=2.6, 8.4 Hz), 7.19-7.24 (m, 5H), 7.27-7.32 (m, 2H).

SYNTHESIS EXAMPLE 7

2-Benzyl-8-methoxybenzo[f]quinoxalin-3-yl)acetamide (11)

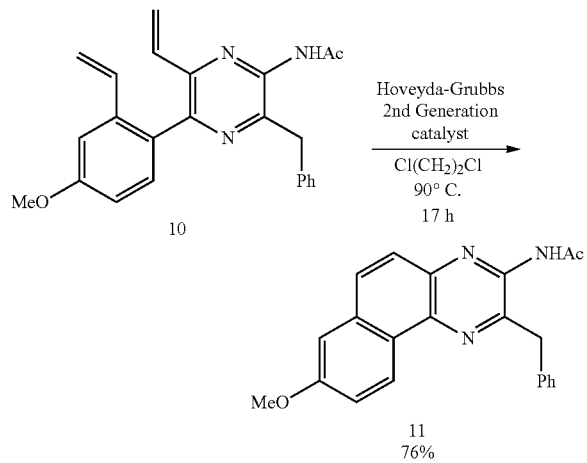

Under an argon atmosphere, to a solution of Hoveyda-Grubbs second generation catalyst (61.3 mg, 97.8 μmol) in 1,2-dichloromethane (150 mL) was added N-(3-benzyl-5-(4-methoxy-2-vinylphenyl)-6-vinylpyrazin-2-yl)acetamide (10) (348 mg, 903 μmol) at room temperature. The mixture was then heated to 90° C. and stirred overnight (17 hours). After cooling to room temperature and concentration under reduced pressure, the residue was purified by silica gel flash column chromatography (n-hexane/ethyl acetate=4/3→1/1) to give N-(2-benzyl-8-methoxybenzo[f]quinoxalin-3-yl)acetamide (11) (277 mg, 775 μmol, 85.8%) as a white solid. TLC $R_f$=0.27 (n-hexane/ethyl acetate=1/1); $^1$H NMR. (400 MHz, CDCl$_3$) δ 2.33 (s, 3H), 4.00 (s, 3H), 4.50 (s, 2H), 7.24-7.34 (m, 5H), 7.38 (dd, 1H, J=2.6, 8.8 Hz), 7.42 (br, 1H), 7.90 (d, 1H, J=8.8 Hz), 7.93 (d, 1H, J=8.8 Hz), 9.01 (d, 1H, J=8.8 Hz).

SYNTHESIS EXAMPLE 8

N-(2-Benzyl-8-hydroxybenzo[f]quinoxalin-3-yl)acetamide (13)

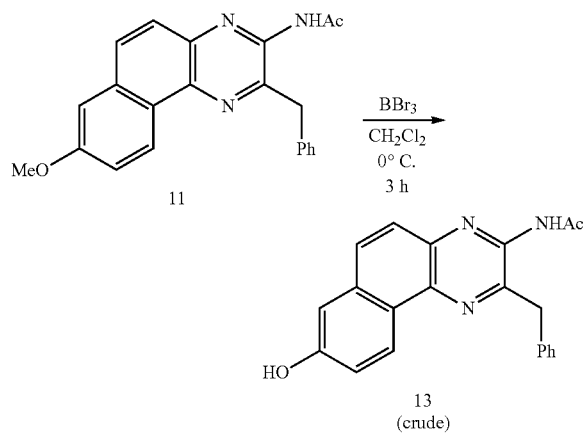

Under an argon atmosphere, to a suspension of N-(2-benzyl-8-methoxybenzo[f]quinoxalin-3-yl)acetamide (60.0 mg, 168 μmol) in anhydrous dichloromethane (2 mL) was added boron trifluoride (1.0 M in dichloromethane) (840 μL, 840 μmol) at 0° C. After elevating to room temperature, the mixture was stirred for 3 hours. To the mixture was then added a solution of saturated sodium hydrogencarbonate, and the product was extracted with ethyl acetate (×3). The combined organic extract was washed successively with water (×1) and brine (×1), followed by drying over anhydrous sodium sulfate. Filtration and concentration under reduced pressure gave N-(2-benzyl-8-hydroxybenzo[f]quinoxalin-3-yl)acetamide (13) as a crude yellow solid product. The product was used for the subsequent reaction without any further purification. TLC $R_f$=0.36 (n-hexane/ethyl acetate=1/2); $^1$H NMR (500 MHz, CD$_3$OD) δ 2.17 (s, 3H), 4.50 (s, 2H), 7.20-7.32 (m, 9H), 7.78 (d, 1H, J=9.0 Hz), 7.96 (d, 1H, J=9.0 Hz), 9.44 (d, 1H, J=7.5 Hz).

SYNTHESIS EXAMPLE 9

3-Amino-2-benzylbenzo[f]quinoxalin-8-ol (14, v-coelenteramine)

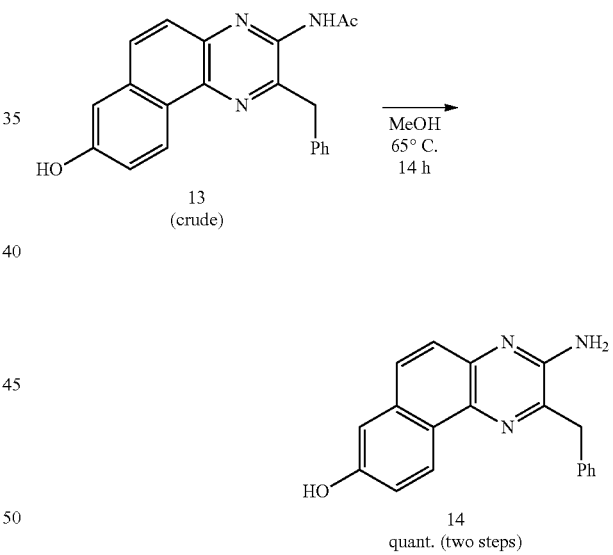

A solution of the obtained crude product of N-(2-benzyl-8-hydroxybenzo[f]quinoxalin-3-yl)acetamide (13) in methanol (20 mL) was heated to 65° C. and stirred overnight (14 hours). After cooling to room temperature, the solution was concentrated under reduced pressure and the residue was purified by silica gel flash column chromatography (n-hexane/ethyl acetate=1/1→1/10) to give 3-amino-2-benzylbenzo[f]quinoxalin-8-ol (14, v-coelenteramine) (51.3 mg, 170 mmol, quant., two steps) as an ocherous solid. TLC $R_f$=0.34 (n-hexane/ethyl acetate=1/1); $^1$H NMR (500 MHz, CD$_3$OD) δ 4.33 (s, 2H), 7.16-7.20 (m, 2H), 7.21-7.26 (m, 1H), 7.30-7.38 (m, 5H), 7.50 (d, 1H, J=9.0 Hz), 7.76 (d, 1H, J=9.0 Hz), 8.77 (d, 1H, J=9.0 Hz).

SYNTHESIS EXAMPLE 10

3-Amino-2-benzyl-8-methoxybenzo[f]quinoxaline (12)

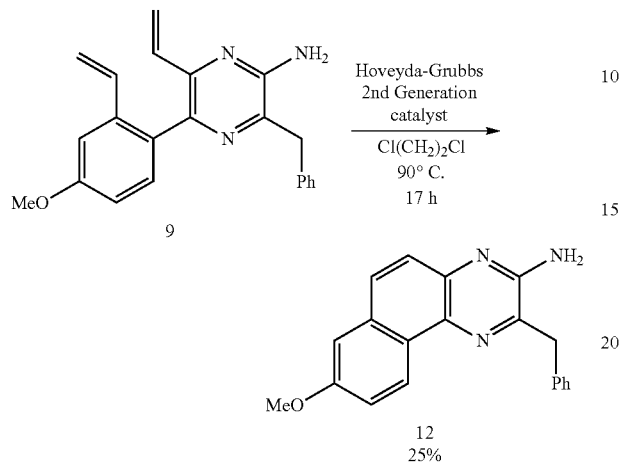

Under an argon atmosphere, to a solution of Hoveyda-Grubbs second generation catalyst (84.5 mg, 135 µmol) in 1,2-dichloroethane (100 mL) was added 2-amino-3-benzyl-5-(4-methoxy-2-vinylphenyl)-6-vinylpyrazine (9) (585 mg, 1.70 mmol) at room temperature. The mixture was then heated to 90° C. and stirred overnight (17 hours). After cooling to room temperature, the mixture was concentrated under reduced pressure. The residue was purified by silica gel flash column chromatography (n-hexane/ethyl acetate=3/1→2/1) to give 3-amino-2-benzyl-8-methoxybenzo[f]quinoxaline (12) as a white solid (136 mg, 431 µmol, 25.3%). TLC $R_f$=0.64 (n-hexane/ethyl acetate=1/1); $^1$H NMR (500 MHz, CDCl$_3$) δ 3.98 (s, 3H), 4.39 (s, 2H), 4.63 (s, 2H), 7.21-7.38 (m, 7H), 7.63 (d, 1H, J=9.0 Hz), 7.85 (d, 1H, J=9.0 Hz), 9.00 (d, 1H, J=9.0 Hz); $^{13}$C NMR (126 MHz, CDCl$_3$) δ 41.8, 55.4, 107.5, 118.1, 124.9, 125.5, 125.8, 127.2, 128.7 (2C), 129.1 (2C), 130.1, 132.7, 134.6, 136.6, 138.9, 143.1, 151.2, 158.5.

SYNTHESIS EXAMPLE 11

3-Amino-2-benzylbenzo[f]quinoxalin-8-ol (14, v-coelenteramine) (synthesis from 12)

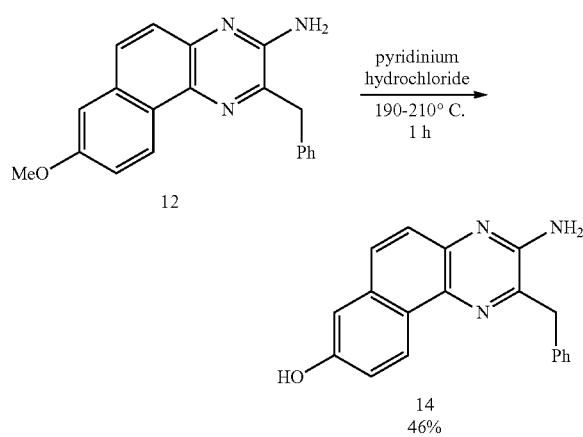

A mixture of 3-amino-2-benzyl-8-methoxybenzo[f]quinoxaline (12) (125 mg, 396 µmol) and pyridinium hydrochloride (2.50 g, 21.6 mmol) was stirred at 190° C. (oil bath temperature) for 30 minutes and at 210° C. (oil bath temperature) for further 30 minutes. After cooling to room temperature, to the mixture was added water, the product was extracted with ethyl acetate (×3). The combined organic extract was washed successively with water (×1) and brine (×1), followed by drying over anhydrous sodium sulfate. After filtration and concentration under reduced pressure, the residue was purified by silica gel flash column chromatography (n-hexane/ethyl acetate=1/1→1/10) to give 3-amino-2-benzylbenzo[f]quinoxalin-8-ol (14, v-coelenteramine) (55.5 mg, 184 µmol, 46.5%) as an ocherous solid.

SYNTHESIS EXAMPLE 12 v-Coelenterazine (2, v-CTZ)

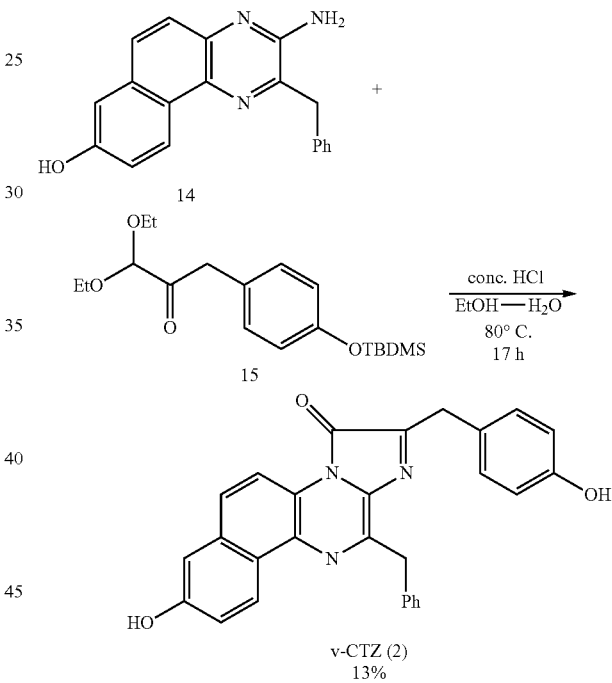

Under an argon atmosphere, to a solution of 3-(4-(tert-butyldimethylsilyloxy)phenyl)-1,1-diethoxypropan-2-one (15) (101 mg, 286 µmol) in ethanol (2 mL) and water (0.4 mL) was added 3-amino-2-benzylbenzo[f]quinoxalin-8-ol (14) (55.5 mg, 184 µmol). After cooling to 0° C., to the mixture was further added conc. hydrochloric acid (0.20 mL). The mixture was heated to 80° C. and stirred overnight (18 hours). After cooling to room temperature and concentration under reduced pressure, the residue was purified by silica gel flash column chromatography (n-hexane/ethyl acetate=1/1→1/2→ethyl acetate alone) in an argon flow to give v-coelenterazine (2, v-CTZ) (10.9 mg, 24.4 µmol, 13.2%) as ocherous powders. TLC $R_f$=0.50 (n-hexane/ethyl acetate=1/1); $^1$H NMR (500 MHz, CD$_3$OD) δ 4.08 (s, 2H), 4.51 (s, 2H), 6.69-6.72 (AA'BB', 2H), 7.17-7.24 (m, 5H), 7.29 (t, 2H, J=7.5 Hz), 7.43 (d, 2H, J=7.5 Hz), 7.63 (d, 1H, J=8.5 Hz), 8.40 (br, 1H), 9.26 (br, 1H).

SYNTHESIS EXAMPLE 13 cf3-v-coelenterazine (17, cf3-v-CTZ)

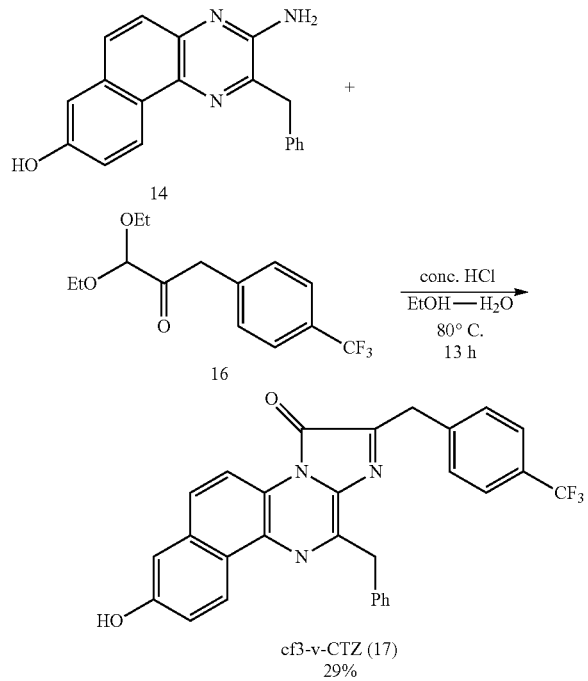

cf3-v-CTZ (17)
29%

Under an argon atmosphere, to a solution of 3-(4-(trifluoromethyl)phenyl)propan-1,1-diethoxy-2-one (16) (86.9 mg, 299 μmol) in ethanol (2 mL) and water (0.2 mL) was added 3-amino-2-benzylbenzo[f]quinoxalin-8-ol (14) (60.2 mg, 200 μmol). After cooling to 0° C., to the mixture was further added conc. hydrochloric acid (0.10 mL). The mixture was heated to 80° C. and stirred overnight (13 hours). After cooling to room temperature and concentration under reduced pressure, the residue was purified by silica gel flash column chromatography (n-hexane/ethyl acetate=1/1→1/2→ethyl acetate alone) in an argon flow to give cf3-v-coelenterazine (17, cf3-v-CTZ) (28.6 mg, 57.3 μmol, 28.7%) as yellow powders. TLC $R_f$=0.24 (n-hexane/ethyl acetate=1/2); $^1$H NMR (500 MHz, $CD_3OD$) δ 4.26 (s, 2H), 4.51 (s, 2H), 7.18-7.25 (m, 3H), 7.28-7.33 (m, 2H), 7.40-7.44 (AA'BB', 2H), 7.54-7.66 (m, 5H), 8.29 (br, 1H), 9.17 (br, 1H).

EXAMPLE 1

Construction of Expression Vector

1) Construction of *Renilla* Luciferase Expression Vector pCold-RL

Novel expression vector pCold-RL was constructed by the following procedures. Using the vector pHis-RL having *Renilla* luciferase gene, described in Inouye & Shimomura, Biochem. Biophys. Res. Commun., 233 (1997) 349-353, as a template, PCR was performed (cycle conditions: 25 cycles; 1 min/94° C., 1 min/50° C., 1 min/72° C.) with a PCR kit (manufactured by Takara Bio Inc.) using two PCR primers, RL-17N/SacI (5' gcc GAGCTC ACT TCG AAA GTT TAT GAT CC 3': SEQ ID NO: 21) and RL-18C/XhoI (5' cgg CTCGAG TTA TTG TTC ATT TTT GAG AA 3': SEQ ID NO: 22). After purification by a PCR purification kit (manufactured by Qiagen Inc.) and digestion with the restriction enzymes SacI and XhoI, the resulting fragment was inserted into the SacI/XhoI restriction enzyme site of vector pCold-II (manufactured by Takara Bio Inc., GenBank: AB 186389) to give *Renilla* luciferase expression vector pCold-RL. The nucleotide sequence of the insert DNA was confirmed by a DNA sequencer (manufactured by ABI Inc.).

2) Construction of Mutant *Renilla* Luciferase-547 Expression Vector pCold-hRL-547 to Shift the Emission to Longer Wavelength The novel expression vector pCold-hRL-547 having mutant *Renilla* luciferase-547 gene (hRL-547) was constructed by the following procedures. The vector pCR2.1-hRL-547 plasmid having mutant *Renilla* luciferase-547 gene was constructed by the chemical synthesis and PCR procedures. The mutant *Renilla* luciferase-547 gene was constructed as follows: the construction of pCR2.1-hRL-547 involved designing based on RLuc8.6-547 described in Nature Methods, 4 (2007) 641-643, synthesizing by a combination of conventional chemical synthesis with PCR (Operon Inc.) and cloning into the Asp718/EcoRI restriction enzyme site of pCR2.1 (Invitrogen Inc.). In order to construct the pCold-hRL-547 vector, pCR2.1-hRL-547 was digested with restriction enzymes Asp718/EcoRI and inserted into the Asp718/EcoRI restriction enzyme site of vector pCold-II to construct *Renilla* luciferase-547 expression vector pCold-hRL-547. The nucleotide sequence of the insert DNA was confirmed with a DNA sequencer (manufactured by ABI Inc.).

The nucleotide sequence of DNA encoding hRL-547 is shown by SEQ ID NO: 19. The amino acid sequence of hRL-547 is shown by SEQ ID NO: 20.

EXAMPLE 2

Purification of Recombinant Protein

1) Expression of Recombinant Protein in *Escherichia coli*

To express the recombinant protein in *Escherichia coli*, *Renilla* luciferase gene expression vector pCold-RL and *Renilla* luciferase-547 gene expression vector pCold-hRL-547 were used. The vectors were transformed into *Escherichia coli* BL21 and the resulting transformants were cultured in 10 mL of LB liquid medium (10 g of bactotryptone, 5 g of yeast extract and 5 g of sodium chloride, per liter of water, pH 7.2) supplemented with ampicillin (50 μg/m) and cultured at 37° C. for 16 hours. The cultured LB broth was added to a fresh LB liquid medium of 400 mL×5 (2 L in total) followed by incubation at 37° C. for 4.5 hours. After cooling on ice for an hour, 0.2 mM IPTG was added and incubation was continued at 15° C. for 17 hours. After completion of the incubation, the cells were harvested by centrifugation (5,000 rpm, 5 minutes) and used as the starting material for protein extraction.

2) Extraction of Recombinant Protein from Cultured Cells and Nickel Chelate Gel Column Chromatography The culture cells collected were suspended in 200 mL of 50 mM Tris-HCl (pH7.6). Under cooling on ice, the cells were disrupted by ultrasonication (manufactured by Branson, Sonifier Model Cycle 250) 3 times each for 3 minutes. The cell lysate was centrifuged at 10,000 rpm (12,000×g) at 4° C. for 20 minutes. The soluble fractions obtained were applied onto a nickel-chelate column (Amersham Bioscience, column size: diameter 2.5×6.5 cm) to adsorb the recombinant protein. After washing with 500 mL of 50 mM Tris-HCl (pH 7.6), the objective recombinant protein was eluted with 50 mM Tris-HCl (pH 7.6) containing 0.1M imidazole (manufactured by Wako Pure Chemical Industry). Protein concentration was determined using a commercially available kit (manufactured by Bio-Rad) by the method of Bradford and using bovine serum albumin (manufactured by Pierce) as a standard. The yields in the purification process are shown in TABLE 1.

TABLE 1 shows the purification yields of *Renilla* luciferase and *Renilla* luciferase-547.

TABLE 1

| Purification Process | Total Volume (mL) | Total Protein (mg) (%) | Total Activity ($\times 10^8$ rlu) (%) | Specific Activity ($\times 10^8$ rlu/mg) |
|---|---|---|---|---|
| 1) *Renilla* luciferase Soluble fraction | 200 | 600 (100) | 1423.0 (100) | 2.37 |
| Dialysis after nickel chelate gel elution | 40 | 117.6 (19.6) | 834.3 (58.6) | 7.09 |
| 2) *Renilla* luciferase-547 Soluble fraction | 200 | 480 (100) | 79.9 (100) | 0.17 |
| Dialysis after nickel chelate gel elution | 58.5 | 83.7 (17.4) | 61.4 (76.9) | 0.73 |

EXAMPLE 3

Measurement of Luminescence Activity

After *Renilla* luciferase (2.94 ng) or *Renilla* luciferase-547 (14.3 ng) was dispensed into a 96-well microplate (manufactured by Nunc) in an amount of 10 µL/well, 0.1 mL of 30 mM Tris-HCl (pH 7.6)-10 mM EDTA containing 0.05 µg of coelenterazine or v-coelenterazine was injected into the wells thereby to initiate the luminescence reaction, and the luminescence intensity was measured using a luminescence plate reader Centro LB960 (manufactured by Berthold). The luminescence intensity was measured for 60 seconds 3 times in 0.1 second intervals, and the maximum luminescence intensity ($I_{max}$) and the mean (rlu) from luminescence integrated for 60 seconds were expressed in terms of relative activity (%) (TABLE 2).

TABLE 2 shows the luminescence activities of *Renilla* luciferase and *Renilla* luciferase-547.

TABLE 2

| | Maximum Luminescence Intensity $I_{max}$ (Int.) (%) | |
|---|---|---|
| Substrate | *Renilla* Luciferase | *Renilla* Luciferase-547 |
| Coelenterazine | 100 (100) | 100 (100) |
| v-Coelenterazine | 71.8 (47.3) | 213 (73.4) |
| cf3-v-Coelenterazine | 18.9 (12.3) | 16.9 (11.9) |

EXAMPLE 4

Measurement of Emission Spectrum

The luminescence reaction was initiated by adding luciferase to 1 mL of 50 mM Tris-HCl (pH 7.6)-10 mM EDTA containing 5 µg (1 µg/µL) of substrate coelenterazine or v-coelenterazine dissolved in ethanol. The protein amounts of luciferases used were *Renilla* luciferase: 1.5 µg and *Renilla* luciferase-547: 7.2 µg in the case of coelenterazine as substrate. On the other hand, the protein amounts in v-coelenterazine as substrate were *Renilla* luciferase: 14.7 µg and *Renilla* luciferase-547: 35.8 µg. Luminescence spectra were measured in a quartz cell with a 10 mm optical path under the conditions of band width: 20 nm, sensitivity: medium, scan speed: 2000 nm/min and 22-25° C., using a fluorescence spectrophotometer FP-6500 (manufactured by JASCO) with the excitation light source turned off. The emission maximum (λmax, m) and half bandwidth (nm) were determined from the spectra measured, which are shown in TABLE 3.

TABLE 3 shows the results of analysis of the emission spectra of *Renilla* luciferase and *Renilla* luciferase-547.

TABLE 3

| | Emission Maximum $\lambda_{max}$ (half bandwidth) (nm) | |
|---|---|---|
| Substrate | *Renilla* luciferase | *Renilla* luciferase-547 |
| Coelenterazine | 485.0 (95) | 547.0 (124) |
| v-Coelenterazine$^a$ | 519.0 (105) | 593.0 (130) |
| cf3-v-Coelenterazine | 525.5 (121) | 599.0 (132) |

As shown in EXAMPLES above, when v-coelenterazine was used as a luminescence substrate, the maximum emission wavelength was shifted toward a longer wavelength side relative to coelenterazine. In addition, when cf3-v-coelenterazine was used as a luminescence substrate, the maximum emission wavelength was shifted toward a longer wavelength side even relative to v-coelenterazine.

SEQUENCE LISTING FREE TEXT

[SEQ ID NO: 1]
This is the nucleotide sequence of native apoaequorin.
[SEQ ID NO: 2]
This is the amino acid sequence of native apoaequorin.
[SEQ ID NO: 3]
This is the nucleotide sequence of native apoclytin-I.
[SEQ ID NO: 4]
This is the amino acid sequence of native apoclytin-I.
[SEQ ID NO: 5]
This is the nucleotide sequence of native apoclytin-II.
[SEQ ID NO: 6]
This is the amino acid sequence of native apoclytin-II.
[SEQ ID NO: 7]
This is the nucleotide sequence of native apomitrocomin.
[SEQ ID NO: 8]
This is the amino acid sequence of native apomitrocomin.
[SEQ ID NO: 9]
This is the nucleotide sequence of native apobelin.
[SEQ ID NO: 10]
This is the amino acid sequence of native apobelin.
[SEQ ID NO: 11]
This is the nucleotide sequence of native apobervoin.
[SEQ ID NO: 12]
This is the amino acid sequence of native apobervoin.
[SEQ ID NO: 13]
This is the nucleotide sequence of *Renilla* luciferase.
[SEQ ID NO: 14]
This is the amino acid sequence of *Renilla* luciferase.
[SEQ ID NO: 15]
This is the nucleotide sequence of *Oplophorus* luciferase.
[SEQ ID NO: 16]
This is the amino acid sequence of *Oplophorus* luciferase.
[SEQ ID NO: 17]
This is the nucleotide sequence of *Gaussia* luciferase.
[SEQ ID NO: 18]
This is the amino acid sequence of *Gaussia* luciferase.
[SEQ ID NO: 19]
This is the nucleotide sequence of *Renilla* luciferase mutant.
[SEQ ID NO: 20]
This is the amino acid sequence of *Renilla* luciferase mutant.

[SEQ ID NO: 21]
This is the nucleotide sequence of PCR primer RL-17N/SacI.

[SEQ ID NO: 22]
This is the nucleotide sequence of PCR primer RL-18C/XhoI

The invention claimed is:

1. A process for producing a v-coelenterazine compound represented by formula (II):

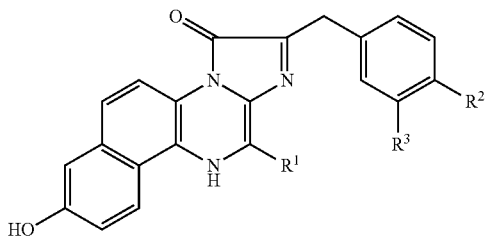

wherein:

R[1] is hydrogen; a halogen; an unsubstituted aryl; an aryl substituted with at least one substituent selected from the group consisting of a halogen, hydroxy, an alkyl having 1 to 6 carbon atoms, an alkoxy having 1 to 6 carbon atoms, an amino and a dialkylamino having 1 to 6 carbon atoms; an unsubstituted arylalkyl; an arylalkyl substituted with at least one substituent selected from the group consisting of a halogen, hydroxy, an alkyl having 1 to 6 carbon atoms, an alkoxy having 1 to 6 carbon atoms, an amino and a dialkylamino having 1 to 6 carbon atoms; an unsubstituted arylalkenyl; an arylalkenyl substituted with at least one substituent selected from the group consisting of a halogen, hydroxy, an alkyl having 1 to 6 carbon atoms, an alkoxy having 1 to 6 carbon atoms, an amino and a dialkylamino having 1 to 6 carbon atoms; an unsubstituted alkyl; an alkyl substituted with an alicyclic group; an unsubstituted alkenyl; an alkenyl substituted with an alicyclic group; an alicyclic group; a heterocyclic group; an unsubstituted alkynyl; or an alkynyl substituted with an alicyclic group, each of R[2] and R[3] independently represents hydrogen, hydroxy, a halogen, an unsubstituted alkyl having 1 to 4 carbons; an alkyl having 1 to 4 carbon atoms substituted with an alicyclic group, trifluoromethyl or an alkoxy, which comprises:

(1) reacting a compound represented by formula (VIII):

wherein R[1] is the same as defined above; and R[4] is a protecting group selected from the group consisting of methyl, methoxymethyl, tetrahydropyranyl, benzyl, 4-methoxybenzyl, tert-butyldimethylsilyl, trimethylsilyl, triethylsilyl, phenyldimethylsilyl, tert-butyldiphenylsilyl, and triisopropylsilyl;

with a methyltriphenylphosphonium salt in the presence of a solvent and a base to give a compound represented by formula (IX):

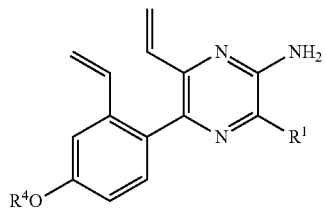

wherein R[1] and R[4] are the same as defined above;

(2) performing a ring-closing metathesis reaction on any one selected from the group consisting of the compound represented by formula (IX) and a compound represented by formula (X) which is prepared by protecting the amino in formula (IX) with R[5]:

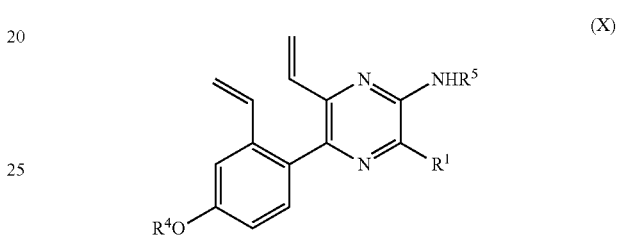

wherein R[1] and R[4] are the same as defined above; and R[5] is a protecting group selected from the group consisting of acetyl, benzoyl, p-tosyl, tert-butoxycarbonyl and benzyloxycarbonyl in the presence of a solvent and a catalyst, and then deprotecting R[4] and, if any, R[5] to give a v-coelenteramine compound represented by formula (XIV):

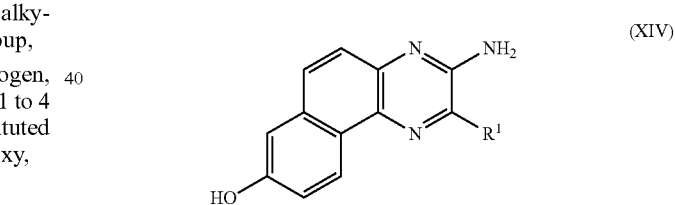

wherein R[1] is the same as defined above; and, (3) reacting the compound represented by formula (XIV) with a compound represented by formula (XV):

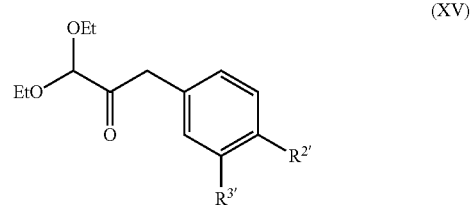

wherein each of R[2'] and R[3'] independently represents hydrogen, hydroxy, an alkoxy, a halogen, a hydrocarbon group, or a hydroxy group protected with a protecting group selected from the group consisting of tert-butyldimethylsilyl, methoxymethyl, tetrahydropyranyl, trimethylsilyl, triethylsilyl, phenyldimethylsilyl, tert-butyldiphenylsilyl, and triisopropylsilyl to give the compound represented by formula (II).

2. The process according to claim 1, wherein at least one base selected from the group consisting of n-butyl lithium, potassium tert-butoxide, sodium methoxide, sodium ethoxide and lithium diisopropylamide is used as the base in step (1).

3. The process according to claim 1, wherein at least one solvent selected from the group consisting of tetrahydrofuran, diethyl ether, cyclopropyl methyl ether, tert-butyl methyl ether, dioxane and toluene is used as the solvent in step (1).

4. The process according to claim 1, wherein the reaction temperature and reaction time in step (1) are set at 0° C. to 40° C. for an hour to 4 hours.

5. The process according to claim 1, wherein a second generation Hoveyda-Grubbs catalyst is used as the catalyst for the ring-closing metathesis reaction in step (2).

6. The process according to claim 1, wherein at least one solvent selected from the group consisting of dichloroethane, dichloromethane, chloroform, trichloroethane, tetrachloroethane, benzene, toluene, xylene, monochlorobenzene, dichlorobenzene, hexane, heptane, octane, tetrahydrofuran, dioxane, diethyl ether, dibutyl ether, diisopropyl ether and dimethoxyethane is used as the solvent for the ring-closing metathesis reaction in step (2).

7. The process according to claim 1, wherein the reaction temperature and reaction time of the ring-closing metathesis reaction in step (2) are set at 25° C. to 110° C. for an hour to 48 hours.

\* \* \* \* \*

```
                             SEQUENCE LISTING

<160> NUMBER OF SEQ ID NOS: 22

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)

<400> SEQUENCE: 1 atg aca agc aaa caa tac tca gtc aag ctt aca tca gac ttc gac aac      48
Met Thr Ser Lys Gln Tyr Ser Val Lys Leu Thr Ser Asp Phe Asp Asn
1               5                   10                  15 cca aga tgg att gga cga cac aag cat atg ttc aat ttc ctt gat gtc      96
Pro Arg Trp Ile Gly Arg His Lys His Met Phe Asn Phe Leu Asp Val
                20                  25                  30 aac cac aat gga aaa atc tct ctt gac gag atg gtc tac aag gca tct     144
Asn His Asn Gly Lys Ile Ser Leu Asp Glu Met Val Tyr Lys Ala Ser
            35                  40                  45 gat att gtc atc aat aac ctt gga gca aca cct gag caa gcc aaa cga     192
Asp Ile Val Ile Asn Asn Leu Gly Ala Thr Pro Glu Gln Ala Lys Arg
        50                  55                  60 cac aaa gat gct gta gaa gcc ttc ttc gga gga gct gga atg aaa tat     240
His Lys Asp Ala Val Glu Ala Phe Phe Gly Gly Ala Gly Met Lys Tyr
65                  70                  75                  80 ggt gtg gaa act gat tgg cct gca tat att gaa gga tgg aaa aaa ttg     288
Gly Val Glu Thr Asp Trp Pro Ala Tyr Ile Glu Gly Trp Lys Lys Leu
                85                  90                  95 gct act gat gaa ttg gag aaa tac gcc aaa aac gaa cca acg ctc atc     336
Ala Thr Asp Glu Leu Glu Lys Tyr Ala Lys Asn Glu Pro Thr Leu Ile
                100                 105                 110 cgt ata tgg ggt gat gct ttg ttt gat atc gtt gac aaa gat caa aat     384
Arg Ile Trp Gly Asp Ala Leu Phe Asp Ile Val Asp Lys Asp Gln Asn
            115                 120                 125 gga gcc att aca ctg gat gaa tgg aaa gca tac acc aaa gct gct ggt     432
Gly Ala Ile Thr Leu Asp Glu Trp Lys Ala Tyr Thr Lys Ala Ala Gly
        130                 135                 140 atc atc caa tca tca gaa gat tgc gag gaa aca ttc aga gtg tgc gat     480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat     528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt     576
Leu Gly Phe Trp Tyr Thr Met Asp Pro Ala Cys Glu Lys Leu Tyr Gly
                180                 185                 190 gga gct gtc ccc taa                                                  591
Gly Ala Val Pro
        195

<210> SEQ ID NO 2
<211> LENGTH: 196
<212> TYPE: PRT
<213> ORGANISM: Aequorea victoria
```

<400> SEQUENCE: 2

```
Met Thr Ser Lys Gln Tyr Ser Val Lys Leu Thr Ser Asp Phe Asp Asn
1               5                   10                  15
Pro Arg Trp Ile Gly Arg His Lys His Met Phe Asn Phe Leu Asp Val
            20                  25                  30
Asn His Asn Gly Lys Ile Ser Leu Asp Glu Met Val Tyr Lys Ala Ser
        35                  40                  45
Asp Ile Val Ile Asn Asn Leu Gly Ala Thr Pro Glu Gln Ala Lys Arg
    50                  55                  60
His Lys Asp Ala Val Glu Ala Phe Phe Gly Ala Gly Met Lys Tyr
65                  70                  75                  80
Gly Val Glu Thr Asp Trp Pro Ala Tyr Ile Glu Gly Trp Lys Lys Leu
                85                  90                  95
Ala Thr Asp Glu Leu Glu Lys Tyr Ala Lys Asn Glu Pro Thr Leu Ile
            100                 105                 110
Arg Ile Trp Gly Asp Ala Leu Phe Asp Ile Val Asp Lys Asp Gln Asn
        115                 120                 125
Gly Ala Ile Thr Leu Asp Glu Trp Lys Ala Tyr Thr Lys Ala Ala Gly
    130                 135                 140
Ile Ile Gln Ser Ser Glu Asp Cys Glu Glu Thr Phe Arg Val Cys Asp
145                 150                 155                 160
Ile Asp Glu Ser Gly Gln Leu Asp Val Asp Glu Met Thr Arg Gln His
                165                 170                 175
Leu Gly Phe Trp Tyr Thr Met Asp Pro Ala Cys Glu Lys Leu Tyr Gly
            180                 185                 190
Gly Ala Val Pro
        195
```

<210> SEQ ID NO 3
<211> LENGTH: 597
<212> TYPE: DNA
<213> ORGANISM: Clytia gregaria
<220> FEATURE:
<221> NAME/KEY: CDS
<222> LOCATION: (1)..(597)

<400> SEQUENCE: 3

```
atg gct gac act gca tca aaa tac gcc gtc aaa ctc aga ccc aac ttc      48
Met Ala Asp Thr Ala Ser Lys Tyr Ala Val Lys Leu Arg Pro Asn Phe
1               5                   10                  15 gac aac cca aaa tgg gtc aac aga cac aaa ttt atg ttc aac ttt ttg      96
Asp Asn Pro Lys Trp Val Asn Arg His Lys Phe Met Phe Asn Phe Leu
            20                  25                  30 gac att aac ggc gac gga aaa atc act ttg gat gaa atc gtc tcc aaa     144
Asp Ile Asn Gly Asp Gly Lys Ile Thr Leu Asp Glu Ile Val Ser Lys
        35                  40                  45 gct tcg gat gac att tgc gcc aaa ctt gga gca aca cca gaa cag acc     192
Ala Ser Asp Asp Ile Cys Ala Lys Leu Gly Ala Thr Pro Glu Gln Thr
    50                  55                  60 aaa cgt cac cag gat gct gtc gaa gct ttc ttc aaa aag att ggt atg     240
Lys Arg His Gln Asp Ala Val Glu Ala Phe Phe Lys Lys Ile Gly Met
65                  70                  75                  80 gat tat ggt aaa gaa gtc gaa ttc cca gct ttt gtt gat gga tgg aaa     288
Asp Tyr Gly Lys Glu Val Glu Phe Pro Ala Phe Val Asp Gly Trp Lys
                85                  90                  95 gaa ctg gcc aat tat gac ttg aaa ctt tgg tct caa aac aag aaa tct     336
Glu Leu Ala Asn Tyr Asp Leu Lys Leu Trp Ser Gln Asn Lys Lys Ser
            100                 105                 110
```

| | | |
|---|---|---|
| ttg atc cgc gac tgg gga gaa gct gtt ttc gac att ttt gac aaa gac<br>Leu Ile Arg Asp Trp Gly Glu Ala Val Phe Asp Ile Phe Asp Lys Asp<br>115                          120                        125 | 384 |
| gga agt ggc tca atc agt ttg gac gaa tgg aag gct tat gga cga atc<br>Gly Ser Gly Ser Ile Ser Leu Asp Glu Trp Lys Ala Tyr Gly Arg Ile<br>130                          135                        140 | 432 |
| tct gga atc tgc tca tca gac gaa gac gcc gaa aag acc ttc aaa cat<br>Ser Gly Ile Cys Ser Ser Asp Glu Asp Ala Glu Lys Thr Phe Lys His<br>145                        150                        155                        160 | 480 |
| tgc gat ttg gac aac agt ggc aaa ctt gat gtt gat gag atg acc aga<br>Cys Asp Leu Asp Asn Ser Gly Lys Leu Asp Val Asp Glu Met Thr Arg<br>                          165                        170                        175 | 528 |
| caa cat ttg gga ttc tgg tac acc ttg gac ccc aac gct gat ggt ctt<br>Gln His Leu Gly Phe Trp Tyr Thr Leu Asp Pro Asn Ala Asp Gly Leu<br>            180                        185                        190 | 576 |
| tac ggc aat ttt gtt cct taa<br>Tyr Gly Asn Phe Val Pro<br>            195 | 597 |

<210> SEQ ID NO 4
<211> LENGTH: 198
<212> TYPE: PRT
<213> ORGANISM: Clytia gregaria

<400> SEQUENCE: 4

Met Ala Asp Thr Ala Ser Lys Tyr Ala Val Lys Leu Arg Pro Asn Phe
1                   5                  10                  15

Asp Asn Pro Lys Trp Val Asn Arg His Lys Phe Met Phe Asn Phe Leu
               20                  25                  30

Asp Ile Asn Gly Asp Gly Lys Ile Thr Leu Asp Glu Ile Val Ser Lys
          35                  40                  45

Ala Ser Asp Asp Ile Cys Ala Lys Leu Gly Ala Thr Pro Glu Gln Thr
50                  55                  60

Lys Arg His Gln Asp Ala Val Glu Ala Phe Phe Lys Lys Ile Gly Met
65                   70                  75                  80

Asp Tyr Gly Lys Glu Val Glu Phe Pro Ala Phe Val Asp Gly Trp Lys
               85                  90                  95

Glu Leu Ala Asn Tyr Asp Leu Lys Leu Trp Ser Gln Asn Lys Lys Ser
            100                105                110

Leu Ile Arg Asp Trp Gly Glu Ala Val Phe Asp Ile Phe Asp Lys Asp
        115                  120                125

Gly Ser Gly Ser Ile Ser Leu Asp Glu Trp Lys Ala Tyr Gly Arg Ile
130                   135                  140

Ser Gly Ile Cys Ser Ser Asp Glu Asp Ala Glu Lys Thr Phe Lys His
145                   150                  155                  160

Cys Asp Leu Asp Asn Ser Gly Lys Leu Asp Val Asp Glu Met Thr Arg
              165                170                175

Gln His Leu Gly Phe Trp Tyr Thr Leu Asp Pro Asn Ala Asp Gly Leu
        180                  185                190

Tyr Gly Asn Phe Val Pro
        195

<210> SEQ ID NO 5
<211> LENGTH: 657
<212> TYPE: DNA
<213> ORGANISM: Clytia gregaria
<220> FEATURE:
<221> NAME/KEY: CDS
<222> LOCATION: (1)..(657)

<400> SEQUENCE: 5

```
atg tcg gct tta gct gca aga tca aga ttg caa cgc aca gca aat ttt      48
Met Ser Ala Leu Ala Ala Arg Ser Arg Leu Gln Arg Thr Ala Asn Phe
1               5                   10                  15 cac acc agc ata ctg ttg gct aca gat tca aaa tac gcg gtc aaa ctc      96
His Thr Ser Ile Leu Leu Ala Thr Asp Ser Lys Tyr Ala Val Lys Leu
            20                  25                  30 gat cct gat ttt gca aat cca aaa tgg atc aac aga cac aaa ttt atg     144
Asp Pro Asp Phe Ala Asn Pro Lys Trp Ile Asn Arg His Lys Phe Met
        35                  40                  45 ttc aac ttt ttg gac ata aac ggt aat ggg aaa atc aca tta gat gaa     192
Phe Asn Phe Leu Asp Ile Asn Gly Asn Gly Lys Ile Thr Leu Asp Glu
    50                  55                  60 atc gtc tcc aaa gct tca gac gac att tgt gct aaa ctg gat gca aca     240
Ile Val Ser Lys Ala Ser Asp Asp Ile Cys Ala Lys Leu Asp Ala Thr
65                  70                  75                  80 cca gaa cag acc aaa cgt cac cag gat gct gtt gaa gcg ttt ttc aag     288
Pro Glu Gln Thr Lys Arg His Gln Asp Ala Val Glu Ala Phe Phe Lys
                85                  90                  95 aaa atg ggc atg gat tat ggt aaa gaa gtt gca ttc cca gaa ttt att     336
Lys Met Gly Met Asp Tyr Gly Lys Glu Val Ala Phe Pro Glu Phe Ile
            100                 105                 110 aag gga tgg gaa gag ttg gcc gaa cac gac ttg gaa ctc tgg tct caa     384
Lys Gly Trp Glu Glu Leu Ala Glu His Asp Leu Glu Leu Trp Ser Gln
        115                 120                 125 aac aaa agt aca ttg atc cgt gaa tgg gga gat gct gtt ttc gac att     432
Asn Lys Ser Thr Leu Ile Arg Glu Trp Gly Asp Ala Val Phe Asp Ile
    130                 135                 140 ttc gac aaa gac gca agt ggc tca atc agt tta gac gaa tgg aag gct     480
Phe Asp Lys Asp Ala Ser Gly Ser Ile Ser Leu Asp Glu Trp Lys Ala
145                 150                 155                 160 tac gga cga atc tct gga atc tgt cca tca gac gaa gac gct gag aag     528
Tyr Gly Arg Ile Ser Gly Ile Cys Pro Ser Asp Glu Asp Ala Glu Lys
                165                 170                 175 acg ttc aaa cat tgt gat ttg gac aac agt ggc aaa ctt gat gtt gat     576
Thr Phe Lys His Cys Asp Leu Asp Asn Ser Gly Lys Leu Asp Val Asp
            180                 185                 190 gag atg acc agg caa cat tta ggc ttc tgg tac aca ttg gat cca act     624
Glu Met Thr Arg Gln His Leu Gly Phe Trp Tyr Thr Leu Asp Pro Thr
        195                 200                 205 tct gat ggt ctt tat ggc aat ttt gtt ccc taa                         657
Ser Asp Gly Leu Tyr Gly Asn Phe Val Pro
    210                 215
```

<210> SEQ ID NO 6
<211> LENGTH: 218
<212> TYPE: PRT
<213> ORGANISM: Clytia gregaria

<400> SEQUENCE: 6

```
Met Ser Ala Leu Ala Ala Arg Ser Arg Leu Gln Arg Thr Ala Asn Phe
1               5                   10                  15

His Thr Ser Ile Leu Leu Ala Thr Asp Ser Lys Tyr Ala Val Lys Leu
            20                  25                  30

Asp Pro Asp Phe Ala Asn Pro Lys Trp Ile Asn Arg His Lys Phe Met
        35                  40                  45

Phe Asn Phe Leu Asp Ile Asn Gly Asn Gly Lys Ile Thr Leu Asp Glu
    50                  55                  60
```

```
Ile Val Ser Lys Ala Ser Asp Asp Ile Cys Ala Lys Leu Asp Ala Thr
 65                  70                  75                  80

Pro Glu Gln Thr Lys Arg His Gln Asp Ala Val Glu Ala Phe Phe Lys
                 85                  90                  95

Lys Met Gly Met Asp Tyr Gly Lys Glu Val Ala Phe Pro Glu Phe Ile
            100                 105                 110

Lys Gly Trp Glu Glu Leu Ala Glu His Asp Leu Glu Leu Trp Ser Gln
        115                 120                 125

Asn Lys Ser Thr Leu Ile Arg Glu Trp Gly Asp Ala Val Phe Asp Ile
    130                 135                 140

Phe Asp Lys Asp Ala Ser Gly Ser Ile Ser Leu Asp Glu Trp Lys Ala
145                 150                 155                 160

Tyr Gly Arg Ile Ser Gly Ile Cys Pro Ser Asp Glu Asp Ala Glu Lys
                165                 170                 175

Thr Phe Lys His Cys Asp Leu Asp Asn Ser Gly Lys Leu Asp Val Asp
            180                 185                 190

Glu Met Thr Arg Gln His Leu Gly Phe Trp Tyr Thr Leu Asp Pro Thr
        195                 200                 205

Ser Asp Gly Leu Tyr Gly Asn Phe Val Pro
    210                 215

<210> SEQ ID NO 7
<211> LENGTH: 597
<212> TYPE: DNA
<213> ORGANISM: Mitrocoma cellularia
<220> FEATURE:
<221> NAME/KEY: CDS
<222> LOCATION: (1)..(597)

<400> SEQUENCE: 7 atg tca atg ggc agc aga tac gca gtc aag ctt acg act gac ttt gat      48
Met Ser Met Gly Ser Arg Tyr Ala Val Lys Leu Thr Thr Asp Phe Asp
 1               5                  10                  15 aat cca aaa tgg att gct cga cac aag cac atg ttc aac ttc ctt gac      96
Asn Pro Lys Trp Ile Ala Arg His Lys His Met Phe Asn Phe Leu Asp
                20                  25                  30 atc aat tca aat ggc caa atc aat ctg aat gaa atg gtc cat aag gct     144
Ile Asn Ser Asn Gly Gln Ile Asn Leu Asn Glu Met Val His Lys Ala
            35                  40                  45 tca aac att atc tgc aag aag ctt gga gca aca gaa gaa caa acc aaa     192
Ser Asn Ile Ile Cys Lys Lys Leu Gly Ala Thr Glu Glu Gln Thr Lys
        50                  55                  60 cgt cat caa aag tgt gtc gaa gac ttc ttt ggg gga gct ggt ttg gaa     240
Arg His Gln Lys Cys Val Glu Asp Phe Phe Gly Gly Ala Gly Leu Glu
 65                  70                  75                  80 tat gac aaa gat acc aca tgg cct gag tac atc gaa gga tgg aag agg     288
Tyr Asp Lys Asp Thr Thr Trp Pro Glu Tyr Ile Glu Gly Trp Lys Arg
                85                  90                  95 ttg gct aag act gaa ttg gaa agg cat tca aag aat caa gtc aca ttg     336
Leu Ala Lys Thr Glu Leu Glu Arg His Ser Lys Asn Gln Val Thr Leu
            100                 105                 110 atc cga tta tgg ggt gat gct ttg ttc gac atc att gac aaa gat aga     384
Ile Arg Leu Trp Gly Asp Ala Leu Phe Asp Ile Ile Asp Lys Asp Arg
        115                 120                 125 aat gga tcg gtt tcg tta gac gaa tgg atc cag tac act cat tgt gct     432
Asn Gly Ser Val Ser Leu Asp Glu Trp Ile Gln Tyr Thr His Cys Ala
    130                 135                 140
```

```
ggc atc caa cag tca cgt ggg caa tgc gaa gct aca ttt gca cat tgc    480
Gly Ile Gln Gln Ser Arg Gly Gln Cys Glu Ala Thr Phe Ala His Cys
145                 150                 155                 160 gat tta gat ggt gac ggt aaa ctt gat gtg gac gaa atg aca aga caa    528
Asp Leu Asp Gly Asp Gly Lys Leu Asp Val Asp Glu Met Thr Arg Gln
            165                 170                 175 cat ttg gga ttt tgg tat tcg gtc gac cca act tgt gaa gga ctc tac    576
His Leu Gly Phe Trp Tyr Ser Val Asp Pro Thr Cys Glu Gly Leu Tyr
                180                 185                 190 ggt ggt gct gta cct tat taa                                        597
Gly Gly Ala Val Pro Tyr
            195
```

<210> SEQ ID NO 8
<211> LENGTH: 198
<212> TYPE: PRT
<213> ORGANISM: Mitrocoma cellularia

<400> SEQUENCE: 8

```
Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala
        35                  40                  45

Ser Asn Ile Ile Cys Lys Lys Leu Gly Ala Thr Glu Glu Gln Thr Lys
    50                  55                  60

Arg His Gln Lys Cys Val Glu Asp Phe Phe Gly Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

Asn Gly Ser Val Ser Leu Asp Glu Trp Ile Gln Tyr Thr His Cys Ala
    130                 135                 140

Gly Ile Gln Gln Ser Arg Gly Gln Cys Glu Ala Thr Phe Ala His Cys
145                 150                 155                 160

Asp Leu Asp Gly Asp Gly Lys Leu Asp Val Asp Glu Met Thr Arg Gln
                165                 170                 175

His Leu Gly Phe Trp Tyr Ser Val Asp Pro Thr Cys Glu Gly Leu Tyr
            180                 185                 190

Gly Gly Ala Val Pro Tyr
        195
```

<210> SEQ ID NO 9
<211> LENGTH: 588
<212> TYPE: DNA
<213> ORGANISM: Obelia longissima
<220> FEATURE:
<221> NAME/KEY: CDS
<222> LOCATION: (1)..(588)

<400> SEQUENCE: 9

```
atg tct tca aaa tac gca gtt aaa ctc aag act gac ttt gat aat cca    48
Met Ser Ser Lys Tyr Ala Val Lys Leu Lys Thr Asp Phe Asp Asn Pro
1               5                   10                  15
```

```
cga tgg atc aaa aga cac aag cac atg ttt gat ttc ctc gac atc aat      96
Arg Trp Ile Lys Arg His Lys His Met Phe Asp Phe Leu Asp Ile Asn
            20                  25                  30 gga aat gga aaa atc acc ctc gat gaa att gtg tcc aag gca tct gat     144
Gly Asn Gly Lys Ile Thr Leu Asp Glu Ile Val Ser Lys Ala Ser Asp
        35                  40                  45 gac ata tgt gcc aag ctc gaa gcc aca cca gaa caa aca aaa cgc cat     192
Asp Ile Cys Ala Lys Leu Glu Ala Thr Pro Glu Gln Thr Lys Arg His
50                  55                  60 caa gtt tgt gtt gaa gct ttc ttt aga gga tgt gga atg gaa tat ggt     240
Gln Val Cys Val Glu Ala Phe Phe Arg Gly Cys Gly Met Glu Tyr Gly
65                  70                  75                  80 aaa gaa att gcc ttc cca caa ttc ctc gat gga tgg aaa caa ttg gcg     288
Lys Glu Ile Ala Phe Pro Gln Phe Leu Asp Gly Trp Lys Gln Leu Ala
                85                  90                  95 act tca gaa ctc aag aaa tgg gca aga aac gaa cct act ctc att cgt     336
Thr Ser Glu Leu Lys Lys Trp Ala Arg Asn Glu Pro Thr Leu Ile Arg
            100                 105                 110 gaa tgg gga gat gct gtc ttt gat att ttc gac aaa gat gga agt ggt     384
Glu Trp Gly Asp Ala Val Phe Asp Ile Phe Asp Lys Asp Gly Ser Gly
        115                 120                 125 aca atc act ttg gac gaa tgg aaa gct tat gga aaa atc tct ggt atc     432
Thr Ile Thr Leu Asp Glu Trp Lys Ala Tyr Gly Lys Ile Ser Gly Ile
130                 135                 140 tct cca tca caa gaa gat tgt gaa gcg aca ttt cga cat tgc gat ttg     480
Ser Pro Ser Gln Glu Asp Cys Glu Ala Thr Phe Arg His Cys Asp Leu
145                 150                 155                 160 gac aac agt ggt gac ctt gat gtt gac gag atg aca aga caa cat ctt     528
Asp Asn Ser Gly Asp Leu Asp Val Asp Glu Met Thr Arg Gln His Leu
                165                 170                 175 gga ttc tgg tac act ttg gac cca gaa gct gat ggt ctc tat ggc aac     576
Gly Phe Trp Tyr Thr Leu Asp Pro Glu Ala Asp Gly Leu Tyr Gly Asn
            180                 185                 190 gga gtt ccc taa                                                     588
Gly Val Pro
        195

<210> SEQ ID NO 10
<211> LENGTH: 195
<212> TYPE: PRT
<213> ORGANISM: Obelia longissima

<400> SEQUENCE: 10

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125
```

```
Thr Ile Thr Leu Asp Glu Trp Lys Ala Tyr Gly Lys Ile Ser Gly Ile
        130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 11
<211> LENGTH: 627
<212> TYPE: DNA
<213> ORGANISM: Beroe abyssicola
<220> FEATURE:
<221> NAME/KEY: CDS
<222> LOCATION: (1)..(627)

<400> SEQUENCE: 11 atg act gaa cgt ctg aac gag cag aac aac gag agt tac cgc tac ctg      48
Met Thr Glu Arg Leu Asn Glu Gln Asn Asn Glu Ser Tyr Arg Tyr Leu
1               5                   10                  15 aga agc gtg gga aac cag tgg cag ttc aac gta gag gac ctc cac ccc      96
Arg Ser Val Gly Asn Gln Trp Gln Phe Asn Val Glu Asp Leu His Pro
            20                  25                  30 aag atg ttg tcc cgt ctc tac aag aga ttc gat act ttc gat cta gac     144
Lys Met Leu Ser Arg Leu Tyr Lys Arg Phe Asp Thr Phe Asp Leu Asp
        35                  40                  45 agt gac ggt aag atg gag atg gac gag gtc ttg tac tgg ccc gac agg     192
Ser Asp Gly Lys Met Glu Met Asp Glu Val Leu Tyr Trp Pro Asp Arg
    50                  55                  60 atg agg cag ctg gta aac gct act gat gag cag gtt gag aag atg cgg     240
Met Arg Gln Leu Val Asn Ala Thr Asp Glu Gln Val Glu Lys Met Arg
65                  70                  75                  80 gat gct gtg aga gtt ttc ttt ttg cac aag gga gtg gag cca gta aac     288
Asp Ala Val Arg Val Phe Phe Leu His Lys Gly Val Glu Pro Val Asn
                85                  90                  95 ggt ctc ctc aga gag gac tgg gtg gaa gct aac aga gtc ttc gct gag     336
Gly Leu Leu Arg Glu Asp Trp Val Glu Ala Asn Arg Val Phe Ala Glu
            100                 105                 110 gct gag aga gaa aga gag cga cga gga gaa cct tct ctt atc gca ctt     384
Ala Glu Arg Glu Arg Glu Arg Arg Gly Glu Pro Ser Leu Ile Ala Leu
        115                 120                 125 ctc tcc aac tct tac tac gat gta ctg gat gat gac ggt gat ggt act     432
Leu Ser Asn Ser Tyr Tyr Asp Val Leu Asp Asp Asp Gly Asp Gly Thr
    130                 135                 140 gtt gac gtc gat gaa tta aag acc atg atg aaa gca ttt gat gtg ccc     480
Val Asp Val Asp Glu Leu Lys Thr Met Met Lys Ala Phe Asp Val Pro
145                 150                 155                 160 cag gaa gct gcc tac acc ttc ttc gag aag gca gac act gac aag agt     528
Gln Glu Ala Ala Tyr Thr Phe Phe Glu Lys Ala Asp Thr Asp Lys Ser
                165                 170                 175 gga aag ttg gag aga aca gaa cta gtt cat ctc ttt aga aag ttt tgg     576
Gly Lys Leu Glu Arg Thr Glu Leu Val His Leu Phe Arg Lys Phe Trp
            180                 185                 190 atg gag cct tac gat cca cag tgg gac gga gtc tac gct tat aag tac     624
Met Glu Pro Tyr Asp Pro Gln Trp Asp Gly Val Tyr Ala Tyr Lys Tyr
        195                 200                 205 taa                                                                  627
```

<210> SEQ ID NO 12
<211> LENGTH: 208
<212> TYPE: PRT
<213> ORGANISM: Beroe abyssicola

<400> SEQUENCE: 12

| | | | | | | | | | | | | | | |
|---|---|---|---|---|---|---|---|---|---|---|---|---|---|---|
| Met | Thr | Glu | Arg | Leu | Asn | Glu | Gln | Asn | Asn | Glu | Ser | Tyr | Arg | Tyr | Leu |
| 1 | | | | 5 | | | | | 10 | | | | | 15 | |
| Arg | Ser | Val | Gly | Asn | Gln | Trp | Gln | Phe | Asn | Val | Glu | Asp | Leu | His | Pro |
| | | | 20 | | | | | 25 | | | | | 30 | | |
| Lys | Met | Leu | Ser | Arg | Leu | Tyr | Lys | Arg | Phe | Asp | Thr | Phe | Asp | Leu | Asp |
| | | | | 35 | | | | | 40 | | | | | 45 | |
| Ser | Asp | Gly | Lys | Met | Glu | Met | Asp | Glu | Val | Leu | Tyr | Trp | Pro | Asp | Arg |
| | 50 | | | | | 55 | | | | | 60 | | | | |
| Met | Arg | Gln | Leu | Val | Asn | Ala | Thr | Asp | Glu | Gln | Val | Glu | Lys | Met | Arg |
| 65 | | | | | 70 | | | | | 75 | | | | | 80 |
| Asp | Ala | Val | Arg | Val | Phe | Phe | Leu | His | Lys | Gly | Val | Glu | Pro | Val | Asn |
| | | | | 85 | | | | | 90 | | | | | 95 | |
| Gly | Leu | Leu | Arg | Glu | Asp | Trp | Val | Glu | Ala | Asn | Arg | Val | Phe | Ala | Glu |
| | | | 100 | | | | | 105 | | | | | 110 | | |
| Ala | Glu | Arg | Glu | Arg | Glu | Arg | Gly | Glu | Pro | Ser | Leu | Ile | Ala | Leu |
| | | | 115 | | | | | 120 | | | | | 125 | | |
| Leu | Ser | Asn | Ser | Tyr | Tyr | Asp | Val | Leu | Asp | Asp | Gly | Asp | Gly | Thr |
| | 130 | | | | | 135 | | | | | 140 | | | | |
| Val | Asp | Val | Asp | Glu | Leu | Lys | Thr | Met | Met | Lys | Ala | Phe | Asp | Val | Pro |
| 145 | | | | | 150 | | | | | 155 | | | | | 160 |
| Gln | Glu | Ala | Ala | Tyr | Thr | Phe | Phe | Glu | Lys | Ala | Asp | Thr | Asp | Lys | Ser |
| | | | | 165 | | | | | 170 | | | | | 175 | |
| Gly | Lys | Leu | Glu | Arg | Thr | Glu | Leu | Val | His | Leu | Phe | Arg | Lys | Phe | Trp |
| | | | 180 | | | | | 185 | | | | | 190 | | |
| Met | Glu | Pro | Tyr | Asp | Pro | Gln | Trp | Asp | Gly | Val | Tyr | Ala | Tyr | Lys | Tyr |
| | | | 195 | | | | | 200 | | | | | 205 | | |

<210> SEQ ID NO 13
<211> LENGTH: 936
<212> TYPE: DNA
<213> ORGANISM: Renilla reniformis
<220> FEATURE:
<221> NAME/KEY: CDS
<222> LOCATION: (1)..(936)

<400> SEQUENCE: 13

```
atg act tcg aaa gtt tat gat cca gaa caa agg aaa cgg atg ata act      48
Met Thr Ser Lys Val Tyr Asp Pro Glu Gln Arg Lys Arg Met Ile Thr
 1               5                  10                  15 ggt ccg cag tgg tgg gcc aga tgt aaa caa atg aat gtt ctt gat tca      96
Gly Pro Gln Trp Trp Ala Arg Cys Lys Gln Met Asn Val Leu Asp Ser
             20                  25                  30 ttt att aat tat tat gat tca gaa aaa cat gca gaa aat gct gtt att     144
Phe Ile Asn Tyr Tyr Asp Ser Glu Lys His Ala Glu Asn Ala Val Ile
         35                  40                  45 ttt tta cat ggt aac gcg gcc tct tct tat tta tgg cga cat gtt gtg     192
Phe Leu His Gly Asn Ala Ala Ser Ser Tyr Leu Trp Arg His Val Val
     50                  55                  60 cca cat att gag cca gta gcg cgg tgt att ata cca gat ctt att ggt     240
Pro His Ile Glu Pro Val Ala Arg Cys Ile Ile Pro Asp Leu Ile Gly
 65                  70                  75                  80
```

-continued

```
atg ggc aaa tca ggc aaa tct ggt aat ggt tct tat agg tta ctt gat      288
Met Gly Lys Ser Gly Lys Ser Gly Asn Gly Ser Tyr Arg Leu Leu Asp
            85                  90                  95 cat tac aaa tat ctt act gca tgg ttt gaa ctt ctt aat tta cca aag      336
His Tyr Lys Tyr Leu Thr Ala Trp Phe Glu Leu Leu Asn Leu Pro Lys
        100                 105                 110 aag atc att ttt gtc ggc cat gat tgg ggt gct tgt ttg gca ttt cat      384
Lys Ile Ile Phe Val Gly His Asp Trp Gly Ala Cys Leu Ala Phe His
    115                 120                 125 tat agc tat gag cat caa gat aag atc aaa gca ata gtt cac gct gaa      432
Tyr Ser Tyr Glu His Gln Asp Lys Ile Lys Ala Ile Val His Ala Glu
130                 135                 140 agt gta gta gat gtg att gaa tca tgg gat gaa tgg cct gat att gaa      480
Ser Val Val Asp Val Ile Glu Ser Trp Asp Glu Trp Pro Asp Ile Glu
145                 150                 155                 160 gaa gat att gcg ttg atc aaa tct gaa gaa gga gaa aaa atg gtt ttg      528
Glu Asp Ile Ala Leu Ile Lys Ser Glu Glu Gly Glu Lys Met Val Leu
                165                 170                 175 gag aat aac ttc ttc gtg gaa acc atg ttg cca tca aaa atc atg aga      576
Glu Asn Asn Phe Phe Val Glu Thr Met Leu Pro Ser Lys Ile Met Arg
            180                 185                 190 aag tta gaa cca gaa gaa ttt gca gca tat ctt gaa cca ttc aaa gag      624
Lys Leu Glu Pro Glu Glu Phe Ala Ala Tyr Leu Glu Pro Phe Lys Glu
        195                 200                 205 aaa ggt gaa gtt cgt cgt cca aca tta tca tgg cct cgt gaa atc ccg      672
Lys Gly Glu Val Arg Arg Pro Thr Leu Ser Trp Pro Arg Glu Ile Pro
    210                 215                 220 tta gta aaa ggt ggt aaa cct gac gtt gta caa att gtt agg aat tat      720
Leu Val Lys Gly Gly Lys Pro Asp Val Val Gln Ile Val Arg Asn Tyr
225                 230                 235                 240 aat gct tat cta cgt gca agt gat gat tta cca aaa atg ttt att gaa      768
Asn Ala Tyr Leu Arg Ala Ser Asp Asp Leu Pro Lys Met Phe Ile Glu
                245                 250                 255 tcg gat cca gga ttc ttt tcc aat gct att gtt gaa ggc gcc aag aag      816
Ser Asp Pro Gly Phe Phe Ser Asn Ala Ile Val Glu Gly Ala Lys Lys
            260                 265                 270 ttt cct aat act gaa ttt gtc aaa gta aaa ggt ctt cat ttt tcg caa      864
Phe Pro Asn Thr Glu Phe Val Lys Val Lys Gly Leu His Phe Ser Gln
        275                 280                 285 gaa gat gca cct gat gaa atg gga aaa tat atc aaa tcg ttc gtt gag      912
Glu Asp Ala Pro Asp Glu Met Gly Lys Tyr Ile Lys Ser Phe Val Glu
    290                 295                 300 cga gtt ctc aaa aat gaa caa taa                                      936
Arg Val Leu Lys Asn Glu Gln
305                 310

<210> SEQ ID NO 14
<211> LENGTH: 311
<212> TYPE: PRT
<213> ORGANISM: Renilla reniformis

<400> SEQUENCE: 14

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60
```

```
Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 15
<211> LENGTH: 591
<212> TYPE: DNA
<213> ORGANISM: Oplophorus gracilorostris
<220> FEATURE:
<221> NAME/KEY: CDS
<222> LOCATION: (1)..(591)

<400> SEQUENCE: 15 atg gcg tac tcc act ctg ttc ata att gca ttg acc gcc gtt gtc act      48
Met Ala Tyr Ser Thr Leu Phe Ile Ile Ala Leu Thr Ala Val Val Thr
  1               5                  10                  15 caa gct tcc tca act caa aaa tct aac cta act ttt acg ttg gca gat      96
Gln Ala Ser Ser Thr Gln Lys Ser Asn Leu Thr Phe Thr Leu Ala Asp
             20                  25                  30 ttc gtt gga gac tgg caa cag aca gct gga tac aac caa gat caa gtg     144
Phe Val Gly Asp Trp Gln Gln Thr Ala Gly Tyr Asn Gln Asp Gln Val
         35                  40                  45 tta gaa caa gga gga ttg tct agt ctg ttc caa gcc ctg gga gtg tca     192
Leu Glu Gln Gly Gly Leu Ser Ser Leu Phe Gln Ala Leu Gly Val Ser
     50                  55                  60 gtc acg ccc ata cag aaa gtt gta ctg tct ggg gag aat ggg tta aaa     240
Val Thr Pro Ile Gln Lys Val Val Leu Ser Gly Glu Asn Gly Leu Lys
 65                  70                  75                  80
```

```
gct gat att cat gtc ata ata cct tac gag gga ctc agt ggt ttt caa       288
Ala Asp Ile His Val Ile Ile Pro Tyr Glu Gly Leu Ser Gly Phe Gln
             85                  90                  95 atg ggt cta att gaa atg atc ttc aaa gtt gtt tac ccc gtg gat gat       336
Met Gly Leu Ile Glu Met Ile Phe Lys Val Val Tyr Pro Val Asp Asp
            100                 105                 110 cat cat ttc aag att att ctc cat tat ggt aca ctc gtt att gac ggt       384
His His Phe Lys Ile Ile Leu His Tyr Gly Thr Leu Val Ile Asp Gly
            115                 120                 125 gta aca ccc aac atg att gac tac ttt gga aga cct tac cct gga att       432
Val Thr Pro Asn Met Ile Asp Tyr Phe Gly Arg Pro Tyr Pro Gly Ile
130                 135                 140 gct gta ttt gac ggc aag cag atc aca gtt act gga act ctg tgg aac       480
Ala Val Phe Asp Gly Lys Gln Ile Thr Val Thr Gly Thr Leu Trp Asn
145                 150                 155                 160 ggc aac aag atc tat gat gag agg cta atc aac cct gat ggt tca ctc       528
Gly Asn Lys Ile Tyr Asp Glu Arg Leu Ile Asn Pro Asp Gly Ser Leu
                165                 170                 175 ctc ttc aga gtt act atc aat gga gtc acg gga tgg agg ctt tgc gag       576
Leu Phe Arg Val Thr Ile Asn Gly Val Thr Gly Trp Arg Leu Cys Glu
            180                 185                 190 aac att ctt gcc taa                                                    591
Asn Ile Leu Ala
            195

<210> SEQ ID NO 16
<211> LENGTH: 196
<212> TYPE: PRT
<213> ORGANISM: Oplophorus gracilorostris

<400> SEQUENCE: 16

Met Ala Tyr Ser Thr Leu Phe Ile Ile Ala Leu Thr Ala Val Val Thr
1               5                   10                  15

Gln Ala Ser Ser Thr Gln Lys Ser Asn Leu Thr Phe Thr Leu Ala Asp
            20                  25                  30

Phe Val Gly Asp Trp Gln Gln Thr Ala Gly Tyr Asn Gln Asp Gln Val
        35                  40                  45

Leu Glu Gln Gly Gly Leu Ser Ser Leu Phe Gln Ala Leu Gly Val Ser
    50                  55                  60

Val Thr Pro Ile Gln Lys Val Val Leu Ser Gly Glu Asn Gly Leu Lys
65                  70                  75                  80

Ala Asp Ile His Val Ile Ile Pro Tyr Glu Gly Leu Ser Gly Phe Gln
                85                  90                  95

Met Gly Leu Ile Glu Met Ile Phe Lys Val Val Tyr Pro Val Asp Asp
            100                 105                 110

His His Phe Lys Ile Ile Leu His Tyr Gly Thr Leu Val Ile Asp Gly
        115                 120                 125

Val Thr Pro Asn Met Ile Asp Tyr Phe Gly Arg Pro Tyr Pro Gly Ile
    130                 135                 140

Ala Val Phe Asp Gly Lys Gln Ile Thr Val Thr Gly Thr Leu Trp Asn
145                 150                 155                 160

Gly Asn Lys Ile Tyr Asp Glu Arg Leu Ile Asn Pro Asp Gly Ser Leu
                165                 170                 175

Leu Phe Arg Val Thr Ile Asn Gly Val Thr Gly Trp Arg Leu Cys Glu
            180                 185                 190

Asn Ile Leu Ala
            195
```

<210> SEQ ID NO 17
<211> LENGTH: 558
<212> TYPE: DNA
<213> ORGANISM: Gaussia princeps
<220> FEATURE:
<221> NAME/KEY: CDS
<222> LOCATION: (1)..(558)

<400> SEQUENCE: 17

```
atg gga gtc aaa gtt ctg ttt gcc ctg atc tgc atc gct gtg gcc gag        48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc        96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc       144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc       192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc       240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc       288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc       336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag       384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc       432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg       480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg       528
Leu Pro Gln Arg Cys Ala Thr Phe Ala Ser Lys Ile Gln Gly Gln Val
                165                 170                 175 gac aag atc aag ggg gcc ggt ggt gac taa                               558
Asp Lys Ile Lys Gly Ala Gly Gly Asp
            180                 185
```

<210> SEQ ID NO 18
<211> LENGTH: 185
<212> TYPE: PRT
<213> ORGANISM: Gaussia princeps

<400> SEQUENCE: 18

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60
```

```
Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
             100                 105                 110

Val Asp Ile Pro Glu Ile Pro Gly Phe Lys Asp Leu Glu Pro Met Glu
         115                 120                 125

Gln Phe Ile Ala Gln Val Asp Leu Cys Val Asp Cys Thr Thr Gly Cys
     130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                 165                 170                 175

Asp Lys Ile Lys Gly Ala Gly Gly Asp
             180                 185

<210> SEQ ID NO 19
<211> LENGTH: 987
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(987)

<400> SEQUENCE: 19 atg aat cac aaa gtg cat cat cat cat cat cat atg gag ctc ggt acc     48
Met Asn His Lys Val His His His His His His Met Glu Leu Gly Thr
 1               5                  10                  15 acc atg gct tcc aag gtg tac gac ccc gag caa cgc aaa cgc atg atc     96
Thr Met Ala Ser Lys Val Tyr Asp Pro Glu Gln Arg Lys Arg Met Ile
             20                  25                  30 act ggg cct cag tgg tgg gct cgc tgc aag caa atg aac gtg ctg gac    144
Thr Gly Pro Gln Trp Trp Ala Arg Cys Lys Gln Met Asn Val Leu Asp
         35                  40                  45 tcc ttc atc aac tac tat gat tcc gag aag cac gcc gag aac gcc gtg    192
Ser Phe Ile Asn Tyr Tyr Asp Ser Glu Lys His Ala Glu Asn Ala Val
     50                  55                  60 att ttt ctg cat ggt aac gct acc tcc agc tac ctg tgg agg cac gtc    240
Ile Phe Leu His Gly Asn Ala Thr Ser Ser Tyr Leu Trp Arg His Val
 65                  70                  75                  80 gtg cct cac atc gag ccc gtg gct aga tgc atc atc cct gat ctg atc    288
Val Pro His Ile Glu Pro Val Ala Arg Cys Ile Ile Pro Asp Leu Ile
                 85                  90                  95 gga atg ggt aag tcc ggc aag agc ggg aat ggc tca tat cgc ctc ctg    336
Gly Met Gly Lys Ser Gly Lys Ser Gly Asn Gly Ser Tyr Arg Leu Leu
            100                 105                 110 gat cac tac aag tac ctc acc gct tgg ttc gag ctg ctg aac ctt cca    384
Asp His Tyr Lys Tyr Leu Thr Ala Trp Phe Glu Leu Leu Asn Leu Pro
        115                 120                 125 aag aaa atc atc ttt gtg ggc cac gac tgg ggg tcc gct ctg gcc ttt    432
Lys Lys Ile Ile Phe Val Gly His Asp Trp Gly Ser Ala Leu Ala Phe
    130                 135                 140 cac tac gcc tac gag cac caa gac agg atc aag gcc atc gtc cat atg    480
His Tyr Ala Tyr Glu His Gln Asp Arg Ile Lys Ala Ile Val His Met
145                 150                 155                 160
```

```
gag agt gtc gtg gac gtg atc gag tcc tgg gcc ggc tgg cct gac atc    528
Glu Ser Val Val Asp Val Ile Glu Ser Trp Ala Gly Trp Pro Asp Ile
            165                 170                 175 gag gag gag gtg gcc ctg atc aag agc gaa gag ggc gag aaa atg gtg    576
Glu Glu Glu Val Ala Leu Ile Lys Ser Glu Glu Gly Glu Lys Met Val
        180                 185                 190 ctt gag aat aac ttc ttc gtc gag acc gtg ctc cca agc aag atc atg    624
Leu Glu Asn Asn Phe Phe Val Glu Thr Val Leu Pro Ser Lys Ile Met
    195                 200                 205 cgg aaa ctg gag cct gag gag ttc gct gcc tac ctg gag cca ttc aag    672
Arg Lys Leu Glu Pro Glu Glu Phe Ala Ala Tyr Leu Glu Pro Phe Lys
210                 215                 220 gag aag ggc gag gtt aga cgg cct acc ctc tcc tgg cct cgc gag atc    720
Glu Lys Gly Glu Val Arg Arg Pro Thr Leu Ser Trp Pro Arg Glu Ile
225                 230                 235                 240 cct ctc gtt aag gga ggc aag ccc gac gtc gtc cag att gtc cgc aac    768
Pro Leu Val Lys Gly Gly Lys Pro Asp Val Val Gln Ile Val Arg Asn
                245                 250                 255 tac aac gcc tac ctt cgg gcc agc gac gat ctg cct aag ctg ttc atc    816
Tyr Asn Ala Tyr Leu Arg Ala Ser Asp Asp Leu Pro Lys Leu Phe Ile
            260                 265                 270 gag tcc gac cct ggg ttc tgg tcc aac gct att gtc gag gga gct aag    864
Glu Ser Asp Pro Gly Phe Trp Ser Asn Ala Ile Val Glu Gly Ala Lys
        275                 280                 285 aag ttc cct aac acc gag ttc gtg aag gtg aag ggc ctc cac ttc ctc    912
Lys Phe Pro Asn Thr Glu Phe Val Lys Val Lys Gly Leu His Phe Leu
    290                 295                 300 cag gag gac gct cca gat gaa atg ggt aag tac atc aag agc ttc gtg    960
Gln Glu Asp Ala Pro Asp Glu Met Gly Lys Tyr Ile Lys Ser Phe Val
305                 310                 315                 320 gag cgc gtg ctg aag aac gag cag taa                                987
Glu Arg Val Leu Lys Asn Glu Gln
                325
```

<210> SEQ ID NO 20
<211> LENGTH: 328
<212> TYPE: PRT
<213> ORGANISM: Artificial sequence
<220> FEATURE:
<223> OTHER INFORMATION: Synthetic Construct

<400> SEQUENCE: 20

```
Met Asn His Lys Val His His His His His Met Glu Leu Gly Thr
1               5                   10                  15

Thr Met Ala Ser Lys Val Tyr Asp Pro Glu Gln Arg Lys Arg Met Ile
            20                  25                  30

Thr Gly Pro Gln Trp Trp Ala Arg Cys Lys Gln Met Asn Val Leu Asp
        35                  40                  45

Ser Phe Ile Asn Tyr Tyr Asp Ser Glu Lys His Ala Glu Asn Ala Val
    50                  55                  60

Ile Phe Leu His Gly Asn Ala Thr Ser Ser Tyr Leu Trp Arg His Val
65                  70                  75                  80

Val Pro His Ile Glu Pro Val Ala Arg Cys Ile Ile Pro Asp Leu Ile
                85                  90                  95

Gly Met Gly Lys Ser Gly Lys Ser Gly Asn Gly Ser Tyr Arg Leu Leu
            100                 105                 110
```

```
Asp His Tyr Lys Tyr Leu Thr Ala Trp Phe Glu Leu Leu Asn Leu Pro
            115                 120                 125

Lys Lys Ile Ile Phe Val Gly His Asp Trp Gly Ser Ala Leu Ala Phe
130                 135                 140

His Tyr Ala Tyr Glu His Gln Asp Arg Ile Lys Ala Ile Val His Met
145                 150                 155                 160

Glu Ser Val Val Asp Val Ile Glu Ser Trp Ala Gly Trp Pro Asp Ile
                165                 170                 175

Glu Glu Glu Val Ala Leu Ile Lys Ser Glu Gly Glu Lys Met Val
            180                 185                 190

Leu Glu Asn Asn Phe Phe Val Glu Thr Val Leu Pro Ser Lys Ile Met
            195                 200                 205

Arg Lys Leu Glu Pro Glu Glu Phe Ala Ala Tyr Leu Glu Pro Phe Lys
210                 215                 220

Glu Lys Gly Glu Val Arg Arg Pro Thr Leu Ser Trp Pro Arg Glu Ile
225                 230                 235                 240

Pro Leu Val Lys Gly Gly Lys Pro Asp Val Val Gln Ile Val Arg Asn
                245                 250                 255

Tyr Asn Ala Tyr Leu Arg Ala Ser Asp Asp Leu Pro Lys Leu Phe Ile
            260                 265                 270

Glu Ser Asp Pro Gly Phe Trp Ser Asn Ala Ile Val Glu Gly Ala Lys
            275                 280                 285

Lys Phe Pro Asn Thr Glu Phe Val Lys Val Lys Gly Leu His Phe Leu
            290                 295                 300

Gln Glu Asp Ala Pro Asp Glu Met Gly Lys Tyr Ile Lys Ser Phe Val
305                 310                 315                 320

Glu Arg Val Leu Lys Asn Glu Gln
                325

<210> SEQ ID NO 21
<211> LENGTH: 29
<212> TYPE: DNA
<213> ORGANISM: Artificial sequence
<220> FEATURE:
<223> OTHER INFORMATION: synthetic DNA

<400> SEQUENCE: 21
gccgagctca cttcgaaagt ttatgatcc                                    29

<210> SEQ ID NO 22
<211> LENGTH: 29
<212> TYPE: DNA
<213> ORGANISM: Artificial sequence
<220> FEATURE:
<223> OTHER INFORMATION: synthetic DNA

<400> SEQUENCE: 22
cggctcgagt tattgttcat ttttgagaa                                    29
```